US007939261B2

(12) United States Patent
Baker et al.

(10) Patent No.: US 7,939,261 B2
(45) Date of Patent: *May 10, 2011

(54) EXPRESSION PROFILE ALGORITHM AND TEST FOR CANCER PROGNOSIS

(75) Inventors: Joffre B. Baker, Montara, CA (US);
John L. Bryant, Allison Park, PA (US);
Soonmyung Paik, Pittsburgh, PA (US);
Steven Shak, Hillsborough, CA (US)

(73) Assignees: Genomic Health, Inc., Redwood City, CA (US); NSABP Foundation, Inc., Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/406,831

(22) Filed: Mar. 18, 2009

(65) Prior Publication Data
US 2009/0280490 A1 Nov. 12, 2009

Related U.S. Application Data

(63) Continuation of application No. 10/883,303, filed on Jun. 30, 2004, now Pat. No. 7,526,387.

(60) Provisional application No. 60/486,302, filed on Jul. 10, 2003, provisional application No. 60/526,947, filed on Dec. 3, 2003.

(51) Int. Cl.
*C12Q 1/68* (2006.01)
*G06F 19/00* (2006.01)

(52) U.S. Cl. .............................. 435/6; 702/20
(58) Field of Classification Search .................. None
See application file for complete search history.

(56) References Cited

U.S. PATENT DOCUMENTS

| | | | |
|---|---|---|---|
| 4,699,877 A | 10/1987 | Cline et al. |
| 4,968,603 A | 11/1990 | Slamon et al. |
| 5,015,568 A | 5/1991 | Tsujimoto et al. |
| 5,202,429 A | 4/1993 | Tsujimoto et al. |
| 5,459,251 A | 10/1995 | Tsujimoto et al. |
| RE35,491 E | 4/1997 | Cline et al. |
| 5,670,325 A | 9/1997 | Lapidus et al. |
| 5,741,650 A | 4/1998 | Lapidus et al. |
| 5,830,665 A | 11/1998 | Shuber et al. |
| 5,830,753 A | 11/1998 | Coulie et al. |
| 5,858,678 A | 1/1999 | Chinnadurai |
| 5,861,278 A | 1/1999 | Wong et al. |
| 5,928,870 A | 7/1999 | Lapidus et al. |
| 5,952,178 A | 9/1999 | Lapidus et al. |
| 5,952,179 A | 9/1999 | Chinnadurai |
| 5,962,312 A | 10/1999 | Plowman et al. |
| 5,985,553 A | 11/1999 | King et al. |
| 6,020,137 A | 2/2000 | Lapidus et al. |
| 6,100,029 A | 8/2000 | Lapidus et al. |
| 6,143,529 A | 11/2000 | Lapidus et al. |
| 6,146,828 A | 11/2000 | Lapidus et al. |
| 6,171,798 B1 | 1/2001 | Levine et al. |
| 6,203,993 B1 | 3/2001 | Shuber et al. |
| 6,207,401 B1 | 3/2001 | Plowman et al. |
| 6,207,452 B1 | 3/2001 | Govindaswamy |
| 6,214,558 B1 | 4/2001 | Shuber et al. |
| 6,245,523 B1 | 6/2001 | Altieri |
| 6,248,535 B1 | 6/2001 | Danenberg et al. |
| 6,271,002 B1 | 8/2001 | Linsley et al. |
| 6,322,986 B1 | 11/2001 | Ross |
| 6,414,134 B1 | 7/2002 | Reed |
| 6,582,919 B2 | 6/2003 | Danenberg |
| 6,602,670 B2 | 8/2003 | Danenberg |
| 6,618,679 B2 | 9/2003 | Loehrlein et al. |
| 6,620,606 B2 | 9/2003 | Bandman et al. |
| 6,696,558 B2 | 2/2004 | Reed et al. |
| 6,716,575 B2 | 4/2004 | Plowman et al. |
| 6,750,013 B2 | 6/2004 | Gish et al. |
| 6,800,737 B2 | 10/2004 | Altieri |
| 6,943,150 B1 | 9/2005 | Altieri |
| 2002/0004491 A1 | 1/2002 | Xu et al. |
| 2002/0009736 A1 | 1/2002 | Wang |
| 2002/0039764 A1 | 4/2002 | Rosen et al. |
| 2002/0160395 A1 | 10/2002 | Altieri et al. |
| 2003/0073112 A1 | 4/2003 | Zhang et al. |
| 2003/0104499 A1 | 6/2003 | Pressman et al. |
| 2003/0165952 A1 | 9/2003 | Linnarsson et al. |
| 2003/0180791 A1 | 9/2003 | Chinnadurai |
| 2003/0198970 A1 | 10/2003 | Roberts |
| 2003/0198972 A1 | 10/2003 | Erlander et al. |
| 2003/0219771 A1 | 11/2003 | Bevilacqua et al. |
| 2003/0229455 A1 | 12/2003 | Bevilacqua et al. |
| 2004/0009489 A1 | 1/2004 | Golub et al. |
| 2004/0126775 A1 | 7/2004 | Altieri et al. |
| 2004/0133352 A1 | 7/2004 | Bevilacqua et al. |
| 2004/0209290 A1 | 10/2004 | Cobleigh et al. |

FOREIGN PATENT DOCUMENTS

| | | |
|---|---|---|
| EP | 0108564 B1 | 5/1988 |
| EP | 1365034 A2 | 11/2003 |
| WO | 99/02714 | 1/1999 |
| WO | 00/50595 | 8/2000 |
| WO | 00/55173 | 9/2000 |
| WO | 01/70979 | 3/2001 |
| WO | 01/25250 | 4/2001 |
| WO | 01/40466 | 6/2001 |
| WO | 01/55320 | 8/2001 |
| WO | 02/00677 | 1/2002 |

(Continued)

OTHER PUBLICATIONS

Abrahamsen, et al., Towards Quantitative mRNA Analysis in Paraffin-Embedded Tissues Using Real-Time Reverse Transcriptase-Polymerase Chain Reaction, J Mol Diagn. Feb. 2003; 5(1):34-41.
Castiglione, et al., Bcl2, p. 53 and clinical outcome in a series of 138 operable breast cancer patients, Anticancer Res. Sep.-Oct. 1999;19(5C):4555-63.
Nogi, et al., Detection of MUC1 and keratin 19 mRNAs in the bone marrow by quantitative RT-PCR predicts the risk of distant metastasis in breast cancer patients, Breast Cancer. 2003;10(1):74-81.

(Continued)

*Primary Examiner* — John S Brusca
(74) *Attorney, Agent, or Firm* — Paula A. Borden; Bozicevic, Field and Francis LLP

(57) ABSTRACT

The present invention provides a noninvasive, quantitative test for prognosis determination in cancer patients. The test relies on measurements of the tumor levels of certain messenger RNAs (mRNAs). These mRNA levels are inserted into a polynomial formula (algorithm) that yields a numerical recurrence score, which indicates recurrence risk.

29 Claims, 3 Drawing Sheets

FOREIGN PATENT DOCUMENTS

| | | |
|---|---|---|
| WO | 02/06526 | 1/2002 |
| WO | 02/08260 | 1/2002 |
| WO | 02/08261 | 1/2002 |
| WO | 02/08282 | 1/2002 |
| WO | 02/08765 | 1/2002 |
| WO | 02/17852 | 3/2002 |
| WO | 02/46467 | 6/2002 |
| WO | 02/55988 | 7/2002 |
| WO | 02/059377 | 8/2002 |
| WO | 02/068579 | 9/2002 |
| WO | 02/103320 | 12/2002 |
| WO | 03/011897 | 2/2003 |
| WO | 03/083096 | 10/2003 |

OTHER PUBLICATIONS

Van'tveer, et al., Gene expression profiling predicts clincial outcome of breast cancer, Nature. Jan. 31, 2002; 415 (6871):530-6.

Abba et al., Gene expression signature of estrogen receptor a status in breast cancer. BMC Genomics 2005; 6:37.

Bertucci et al., Gene expression profiling of primary breast carcinomas using arrays of candidate genes. Human Molecular Genetics 2000;9(20):2981-91.

Callagy et al., BCL-2 is a prognostic marker in breast cancer independently of the Nottingham Prognostic Index. Clin. Cancer Res. 2006; 12 (8):2468-75.

Chenard, et al.,High levels of stromelysin-3 correlate with poor prognosis in patients with breast carcinoma.

Engel, et al., Correlation between stromelysin-3 mRNA level and outcome of human breast cancer, International Journal of Cancer, vol. 58 Issue 6, Jul. 17, 2006, pp. 830-835.

Fisher et al., Relative worth of estrogen or progesterone receptor and pathologic characteristics of differentiation as indicators of prognosis in node negative breast cancer patients: Findings from national surgical adjuvant breast and bowel project protocol B-06.

Gasparini et al., Expression of bcl-2 protein predicts efficacy of adjuvant treatments in operable node-positive breast cancer. Clinical Cancer Research 1995; 1(189-190):189-98.

Glinsky et al., Microarray analysis identifies a death-from=cancer signature predicting therapy failure in patients with multiple types of cancer. J. Clin. Investigation 2005; 115(6):1503-21.

Kononen et al., Tissue microarrays for high-throughput molecular profiling of tumor specimens. Nature Medicine 1998; 4(7):844-7.

Lah et al., Cathepsin B, a prognostic indicator in lymph node-negative breast carcinoma patients: Comparison with cathespin D, cathespin L, and other clinical indicators. Clinical Cancer Research 2000;6:578-84.

Miyoshi et al., Association of centrosomal kinase STK15/BTAK mRNA expression with chromosomal instability in human breast cancers. Int. J. Cancer 2001; 92:370-3.

Span et al., Survivin is an independent prognostic marker for risk stratification of breast cancer patients. Clinical Chemistry 2004; 50 (11):1986-93.

Stefano et al. Expression levels and clinical-pathological correlations of HER2/neu in primary and metastatic human breast cancer. Ann. N. Y. Acad. Sci. 2004; 1028:463-72.

Stein, et al., The SH2 domain protein GRB-7 is co-amplified, overexpressed and in a tight complex with HER2 in breast cancer.

Tanaka et al., Centrosomal kinase AIK1 is overexpressed in invasive ductal carcinoma of the breast. Cancer Research 1999; 59:2041-4.

Tanaka et al., Expression of survivin and its relationship to loss of apoptosis in breast carcinomas. Clinical Cancer Research 2000; 6:127-34.

Townsend, et al., BAG-1 expression in human breast cancer: interrelationship between BAG-1 RNA, protein, HSC70 expression and clinico-pathological data, Journal of Pathology, 197, (1), 51-59.

Turner et al., BAG-1: A novel biomarker predicting long-term survival in early stage breast cancer. J. Clin. Oncol. 2001;19(4):992-1000.

Urruticoechea et al., Proliferation marker Ki-67 in early breast cancer. J. Clin. Oncology 23:7212-20.

Valkovic, et al., Correlation between vascular endothelial growth factor, angiogenesis, and tumor-associated macrophages in invasive ductal breast carcinoma, Virchows Archiv, vol. 440, No. 6 / Jun. 2002, 583-588.

Van De Vijver et al., A gene-expression signature as a predictor of survival in breast cancer. New Eng. J. Med. 2002; 347(25):1999-2009.

Van'T Veer et al., Gene expression profiling predicts clinical outcome of breast cancer. Nature 2002; 415:530-6.

Bhattacharjee et al., Classification of human lung carcinomas by mRNA expression profiling reveals distinct adenocarcinoma subclasses. PNAS 2001;98(24):13790-5.

Brabender et al., Epidermal growth factor receptor and HER2-neu mRNA expression in non-small cell lung cancer is correlated with survival. Clin Canc Res 2001;7:1850-5.

Cambridge Healthtech Institute, Conference agenda, Enabling molecular profiling with cellular resolution: Microgenomics using homogeneous cell samples. Dec. 2002: 5 pgs.

Ding et al., A high-throughput gene expression analysis technique using competitive PCR and matrix-assisted laser desorption ionization time-of-flight MS. PNAS 2003;100(6):3059-64.

Forozan et al., Comparative genomic hybridization analysis of 38 breast cancer cell lines; A basis for interpreting complementary DNA microarray data. Canc Res 2000;60:4519-25.

Furey et al., Support vector machine classification and validation of cancer tissue samples using microarray expression data. Bioinformatics 2000;16:906-14.

Golub et al., Molecular classification of cancer: Class discovery and class prediction by gene expression monitoring. Science 1999;286:531-7.

Gruvberger et al., Estrogen receptor status in breast cancer is associated with remarkably distinct gene expression patterns. Canc Res 2001;61:5979-84.

Martin et al., Linking gene expression patterns to therapeutic groups in breast cancer. Canc Res 2000;60:2232-8.

Perou et al., Molecular portraits of human breast tumors. Nature 2000;406:747-52.

Ramaswamy et al., Multiclass cancer diagnosis using tumor gene expression signatures. PNAS 2001;98 (26):15149-54.

The Comparative Toxicogenomics Database, NM.sub.—000125. Online, retrieved on Feb. 17, 2008 from <ctd.mdibl.org>.

Van De Vijver, Assessment of the need and appropriate method for testing for the human epidermal growth factor receptor-2 (HER2). Eur J Canc 2001;37:S11-7.

West et al., Predicting the clinical status of human breast cancer by using gene expression profiles. PNAS 2001;98 (20):11462-7.

Yan et al., Dissecting complex epigenetic alterations in breast cancer using CpG island microarrays. Canc Res 2001;61:8375-80.

Yang et al., Badge, Beads Array for the Detection of Gene Expression, a high-throughput diagnostic bioassay. Genome Res 2001;11:1888-98.

Yeang et al., Molecular classification of multiple tumor types. Bioinformatics 2001;17(Suppl. 1):S316-22.

Chenard, et al.,High levels of stromelysisn-3 correlate with poor prognosis in patients with breast carcinoma, International Journal of Cancer vol. 69, pp. 448-451 (1996).

Fisher et al., Relative worth of estrogen or progesterone receptor and pathologic characteristics of differentiation as indicators of prognosis in node negative breast cancer patients: Findings from national surgical adjuvant breast and bowel project protocol B-06, Journal of Clinical Oncology vol. 6, pp. 1076-1087 (1988).

Modlich et al., Predictors of primary breast cancers responsiveness to preoperative Epirubicin/Cyclophosphamide-based chemotherapy: translation of microarray data into clinically useful predictive signatures. J. Translational Medicine 2005;3:32.

Nakopoulou et al., Stromelysin-3 protein expression in invasive breast cancer: Relation to proliferation, cell survival and patients' outcome. Modern Pathology 2002;15(11):1154-61.

Nessling et al., Candidate genes in breast cancer revealed by microarray-based comparative genomic hybridization of archived tissue. Cancer Res. 2005; 65(2):439-47.

Nishidate et al., Genome-wide gene-expression profiles of breast-cancer cells purified with laser microbeam microdissection: identification of genes associated with progression and metastasis. Int. J. Oncol. 2004;25(4):797-819.

Press, et al., HER-2/neu gene amplification characterized by fluorescence in situ hybridization: poor prognosis in node-negative breast carcinomas, J Clin Oncol. Aug. 1997;15(8):2894-904.

Reiner et al., Immunocytochemical localization of estrogen and progesterone receptor and prognosis in human primary breast cancer. Cancer Research 1990;50:7057-61.

Rundle et al., The association between glutathione S-transferase M1 genotype and polycyclic aromatic hydrocarbon-DNA adducts in breast tissue. Cancer Epidemiology, Biomarkers & Prevention 2000;9:1079-85.

Shen et al., Prognostic meta-signature of breast cancer developed by two-stage mixture modeling of microarray data. BMC Genomics 2004; 5:94.

Sheppard, et al. Assessing the Expression of Two Genes Simultaneously in Surgical Specimens Using Polymerase Chain Reaction, Mod Pathol 2000;13(4):401-406.

Slamon et al., Human breast cancer: Correlation of relapse and survival with amplification of the HER-2/neu oncogene. Science 235(4785):177-82, (1987).

Sorlie et al., Gene expression patterns of breast carcinomas distinguish tumor sublcasses with clinical implications. PNAS 2001; 98(19):10869-74.

Stefano et al., Expression levels and clinical-pathological correlations of HER2/neu in primary and metastatic human breast cancer. Ann. N.Y. Acad. Sci. 2004; 1028:463-72.

Stein, et al., The SH2 domain protin GRB-7 is co-amplified, overexpressed in a tight complex with HER2 in breast cancer, EMBO Journal vol. 13, pp. 1331-1340 (1994).

Urruticoechea et al., Proliferation marker Ki-67 in early breat cancer. J. Clin. Oncology 23:7212-20, (2004).

Cobleigh M.A. et al., "Tumor gene expression predicts distant disease-free survival (DDFS) in breast cancer patients with 10 or more positive nodes: High throughput RT-PCR assay of paraffin-embedded tumor tissues" 2003, Retrieved from the Internet:URL:http://prod1.asco.org/ASCOv2/Meetings/Abstracts?&vmview=abst_detail_view&confID=23&abstractID=104115.

Esteban J. et al., "Tumor gene expression and prognosis in breast cancer: Multi-gene RT-PCR assay of paraffin-embedded tissue" 2003, Retrieved from the Internet:URL:http://wvvw.asco.org/ASCOv2/Meetings/Abstracts? &vmview=abst detail_view &confID=23&abstractID=104527.

Look M.P. et al., "Pooled analysis of prognostic impact of urokinase-type plasminogen activator and its inhibitor PAI-1 in 8377 breast cancer patients" 2002, *Journal of the National Cancer Institute*, 94(2):116-128.

Paik S. et al., "A multigene assay to predict recurrence of tamoxifen-treated, node-negative breast cancer" *New England Journal of Medicine*, 2004, 351(27):2817-2826.

Paik S. et al., "Expression of the 21 genes in the Recurrence Score assay and tamoxifen clinical benefit in the NSABP study B-14 of node negative, estrogen receptor positive breast cancer" 2005, J. Clin. Oncol. vol. 23, p. 510.

European Office Action for European application No. 04777383.3, dated Sep. 21, 2010 (7 pages).

```
                            SEQUENCE LISTING

<160> NUMBER OF SEQ ID NOS: 84

<210> SEQ ID NO 1
<211> LENGTH: 21
<212> TYPE: DNA
<213> ORGANISM: Artificial Sequence
<220> FEATURE:
<223> OTHER INFORMATION: PCR primer-probe

<400> SEQUENCE: 1
cagcagatgt ggatcagcaa g                                              21

<210> SEQ ID NO 2
<211> LENGTH: 18
<212> TYPE: DNA
<213> ORGANISM: Artificial Sequence
<220> FEATURE:
<223> OTHER INFORMATION: PCR primer-probe

<400> SEQUENCE: 2
gcatttgcgg tggacgat                                                  18

<210> SEQ ID NO 3
<211> LENGTH: 23
<212> TYPE: DNA
<213> ORGANISM: Artificial Sequence
<220> FEATURE:
<223> OTHER INFORMATION: PCR primer-probe

<400> SEQUENCE: 3
aggagtatga cgagtccggc ccc                                            23

<210> SEQ ID NO 4
<211> LENGTH: 23
<212> TYPE: DNA
<213> ORGANISM: Artificial Sequence
<220> FEATURE:
<223> OTHER INFORMATION: PCR primer-probe
```

<400> SEQUENCE: 4
cgttgtcagc acttggaata caa                                    23

<210> SEQ ID NO 5
<211> LENGTH: 24
<212> TYPE: DNA
<213> ORGANISM: Artificial Sequence
<220> FEATURE:
<223> OTHER INFORMATION: PCR primer-probe

<400> SEQUENCE: 5
gttcaacctc ttcctgtgga ctgt                                   24

<210> SEQ ID NO 6
<211> LENGTH: 26
<212> TYPE: DNA
<213> ORGANISM: Artificial Sequence
<220> FEATURE:
<223> OTHER INFORMATION: PCR primer-probe

<400> SEQUENCE: 6
cccaattaac atgacccggc aaccat                                 26

<210> SEQ ID NO 7
<211> LENGTH: 25
<212> TYPE: DNA
<213> ORGANISM: Artificial Sequence
<220> FEATURE:
<223> OTHER INFORMATION: PCR primer-probe

<400> SEQUENCE: 7
cagatggacc tagtacccac tgaga                                  25

<210> SEQ ID NO 8
<211> LENGTH: 24
<212> TYPE: DNA
<213> ORGANISM: Artificial Sequence
<220> FEATURE:
<223> OTHER INFORMATION: PCR primer-probe

<400> SEQUENCE: 8
cctatgattt aagggcattt ttcc                                   24

<210> SEQ ID NO 9
<211> LENGTH: 22
<212> TYPE: DNA
<213> ORGANISM: Artificial Sequence
<220> FEATURE:
<223> OTHER INFORMATION: PCR primer-probe

<400> SEQUENCE: 9
ttccacgccg aaggacagcg at                                     22

<210> SEQ ID NO 10
<211> LENGTH: 20
<212> TYPE: DNA
<213> ORGANISM: Artificial Sequence
<220> FEATURE:
<223> OTHER INFORMATION: PCR primer-probe

<400> SEQUENCE: 10
ttcaggttgt tgcaggagac                                        20

```
<210> SEQ ID NO 11
<211> LENGTH: 20
<212> TYPE: DNA
<213> ORGANISM: Artificial Sequence
<220> FEATURE:
<223> OTHER INFORMATION: PCR primer-probe

<400> SEQUENCE: 11
catcttcttg ggcacacaat                                              20

<210> SEQ ID NO 12
<211> LENGTH: 27
<212> TYPE: DNA
<213> ORGANISM: Artificial Sequence
<220> FEATURE:
<223> OTHER INFORMATION: PCR primer-probe

<400> SEQUENCE: 12
tgtctccatt attgatcggt tcatgca                                      27

<210> SEQ ID NO 13
<211> LENGTH: 18
<212> TYPE: DNA
<213> ORGANISM: Artificial Sequence
<220> FEATURE:
<223> OTHER INFORMATION: PCR primer-probe

<400> SEQUENCE: 13
tggttcccag ccctgtgt                                                18

<210> SEQ ID NO 14
<211> LENGTH: 19
<212> TYPE: DNA
<213> ORGANISM: Artificial Sequence
<220> FEATURE:
<223> OTHER INFORMATION: PCR primer-probe

<400> SEQUENCE: 14
ctcctccacc ctgggttgt                                               19

<210> SEQ ID NO 15
<211> LENGTH: 28
<212> TYPE: DNA
<213> ORGANISM: Artificial Sequence
<220> FEATURE:
<223> OTHER INFORMATION: PCR primer-probe

<400> SEQUENCE: 15
ctccaagccc agattcagat tcgagtca                                     28

<210> SEQ ID NO 16
<211> LENGTH: 21
<212> TYPE: DNA
<213> ORGANISM: Artificial Sequence
<220> FEATURE:
<223> OTHER INFORMATION: PCR primer-probe

<400> SEQUENCE: 16
tgacaatcag cacacctgca t                                            21

<210> SEQ ID NO 17
<211> LENGTH: 23
<212> TYPE: DNA
<213> ORGANISM: Artificial Sequence
<220> FEATURE:
<223> OTHER INFORMATION: PCR primer-probe
```

-continued

```
<400> SEQUENCE: 17
tgtgactaca gccgtgatcc tta                                          23

<210> SEQ ID NO 18
<211> LENGTH: 20
<212> TYPE: DNA
<213> ORGANISM: Artificial Sequence
<220> FEATURE:
<223> OTHER INFORMATION: PCR primer-probe

<400> SEQUENCE: 18
caggccctct tccgagcggt                                              20

<210> SEQ ID NO 19
<211> LENGTH: 21
<212> TYPE: DNA
<213> ORGANISM: Artificial Sequence
<220> FEATURE:
<223> OTHER INFORMATION: PCR primer-probe

<400> SEQUENCE: 19
tgtctcactg agcgagcaga a                                            21

<210> SEQ ID NO 20
<211> LENGTH: 19
<212> TYPE: DNA
<213> ORGANISM: Artificial Sequence
<220> FEATURE:
<223> OTHER INFORMATION: PCR primer-probe

<400> SEQUENCE: 20
accattgcag ccctgattg                                               19

<210> SEQ ID NO 21
<211> LENGTH: 24
<212> TYPE: DNA
<213> ORGANISM: Artificial Sequence
<220> FEATURE:
<223> OTHER INFORMATION: PCR primer-probe

<400> SEQUENCE: 21
cttgaggacg cgaacagtcc acca                                         24

<210> SEQ ID NO 22
<211> LENGTH: 19
<212> TYPE: DNA
<213> ORGANISM: Artificial Sequence
<220> FEATURE:
<223> OTHER INFORMATION: PCR primer-probe

<400> SEQUENCE: 22
cgtggtgccc ctctatgac                                               19

<210> SEQ ID NO 23
<211> LENGTH: 19
<212> TYPE: DNA
<213> ORGANISM: Artificial Sequence
<220> FEATURE:
<223> OTHER INFORMATION: PCR primer-probe

<400> SEQUENCE: 23
ggctagtggg cgcatgtag                                               19
```

```
<210> SEQ ID NO 24
<211> LENGTH: 19
<212> TYPE: DNA
<213> ORGANISM: Artificial Sequence
<220> FEATURE:
<223> OTHER INFORMATION: PCR primer-probe

<400> SEQUENCE: 24
ctggagatgc tggacgccc                                                19

<210> SEQ ID NO 25
<211> LENGTH: 20
<212> TYPE: DNA
<213> ORGANISM: Artificial Sequence
<220> FEATURE:
<223> OTHER INFORMATION: PCR primer-probe

<400> SEQUENCE: 25
attccaccca tggcaaattc                                               20

<210> SEQ ID NO 26
<211> LENGTH: 22
<212> TYPE: DNA
<213> ORGANISM: Artificial Sequence
<220> FEATURE:
<223> OTHER INFORMATION: PCR primer-probe

<400> SEQUENCE: 26
gatgggattt ccattgatga ca                                            22

<210> SEQ ID NO 27
<211> LENGTH: 22
<212> TYPE: DNA
<213> ORGANISM: Artificial Sequence
<220> FEATURE:
<223> OTHER INFORMATION: PCR primer-probe

<400> SEQUENCE: 27
ccgttctcag ccttgacggt gc                                            22

<210> SEQ ID NO 28
<211> LENGTH: 20
<212> TYPE: DNA
<213> ORGANISM: Artificial Sequence
<220> FEATURE:
<223> OTHER INFORMATION: PCR primer-probe

<400> SEQUENCE: 28
ccatctgcat ccatcttgtt                                               20

<210> SEQ ID NO 29
<211> LENGTH: 20
<212> TYPE: DNA
<213> ORGANISM: Artificial Sequence
<220> FEATURE:
<223> OTHER INFORMATION: PCR primer-probe

<400> SEQUENCE: 29
ggccaccagg gtattatctg                                               20

<210> SEQ ID NO 30
<211> LENGTH: 23
<212> TYPE: DNA
<213> ORGANISM: Artificial Sequence
<220> FEATURE:
<223> OTHER INFORMATION: PCR primer-probe
```

<400> SEQUENCE: 30 ctcccccaccc ttgagaagtg cct                                          23

<210> SEQ ID NO 31
<211> LENGTH: 20
<212> TYPE: DNA
<213> ORGANISM: Artificial Sequence
<220> FEATURE:
<223> OTHER INFORMATION: PCR primer-probe

<400> SEQUENCE: 31
ggcccagctt gaatttttca                                               20

<210> SEQ ID NO 32
<211> LENGTH: 27
<212> TYPE: DNA
<213> ORGANISM: Artificial Sequence
<220> FEATURE:
<223> OTHER INFORMATION: PCR primer-probe

<400> SEQUENCE: 32
aagctatgag gaaagaagt acacgat                                        27

<210> SEQ ID NO 33
<211> LENGTH: 30
<212> TYPE: DNA
<213> ORGANISM: Artificial Sequence
<220> FEATURE:
<223> OTHER INFORMATION: PCR primer-probe

<400> SEQUENCE: 33
tcagccactg gcttctgtca taatcaggag                                    30

<210> SEQ ID NO 34
<211> LENGTH: 20
<212> TYPE: DNA
<213> ORGANISM: Artificial Sequence
<220> FEATURE:
<223> OTHER INFORMATION: PCR primer-probe

<400> SEQUENCE: 34
cccactcagt agccaagtca                                               20

<210> SEQ ID NO 35
<211> LENGTH: 20
<212> TYPE: DNA
<213> ORGANISM: Artificial Sequence
<220> FEATURE:
<223> OTHER INFORMATION: PCR primer-probe

<400> SEQUENCE: 35
cacgcaggtg gtatcagtct                                               20

<210> SEQ ID NO 36
<211> LENGTH: 27
<212> TYPE: DNA
<213> ORGANISM: Artificial Sequence
<220> FEATURE:
<223> OTHER INFORMATION: PCR primer-probe

<400> SEQUENCE: 36
tcaagtaaac gggctgtttt ccaaaca                                       27

```
<210> SEQ ID NO 37
<211> LENGTH: 20
<212> TYPE: DNA
<213> ORGANISM: Artificial Sequence
<220> FEATURE:
<223> OTHER INFORMATION: PCR primer-probe

<400> SEQUENCE: 37
cggtgtgaga agtgcagcaa                                               20

<210> SEQ ID NO 38
<211> LENGTH: 19
<212> TYPE: DNA
<213> ORGANISM: Artificial Sequence
<220> FEATURE:
<223> OTHER INFORMATION: PCR primer-probe

<400> SEQUENCE: 38
cctctcgcaa gtgctccat                                                19

<210> SEQ ID NO 39
<211> LENGTH: 24
<212> TYPE: DNA
<213> ORGANISM: Artificial Sequence
<220> FEATURE:
<223> OTHER INFORMATION: PCR primer-probe

<400> SEQUENCE: 39
ccagaccata gcacactcgg gcac                                          24

<210> SEQ ID NO 40
<211> LENGTH: 19
<212> TYPE: DNA
<213> ORGANISM: Artificial Sequence
<220> FEATURE:
<223> OTHER INFORMATION: PCR primer-probe

<400> SEQUENCE: 40
cggactttgg gtgcgactt                                                19

<210> SEQ ID NO 41
<211> LENGTH: 24
<212> TYPE: DNA
<213> ORGANISM: Artificial Sequence
<220> FEATURE:
<223> OTHER INFORMATION: PCR primer-probe

<400> SEQUENCE: 41
ttacaactct tccactggga cgat                                          24

<210> SEQ ID NO 42
<211> LENGTH: 23
<212> TYPE: DNA
<213> ORGANISM: Artificial Sequence
<220> FEATURE:
<223> OTHER INFORMATION: PCR primer-probe

<400> SEQUENCE: 42
ccacttgtcg aaccaccgct cgt                                           23

<210> SEQ ID NO 43
<211> LENGTH: 18
<212> TYPE: DNA
<213> ORGANISM: Artificial Sequence
<220> FEATURE:
<223> OTHER INFORMATION: PCR primer-probe
```

<400> SEQUENCE: 43
gccgagatcg ccaagatg                                           18

<210> SEQ ID NO 44
<211> LENGTH: 27
<212> TYPE: DNA
<213> ORGANISM: Artificial Sequence
<220> FEATURE:
<223> OTHER INFORMATION: PCR primer-probe

<400> SEQUENCE: 44
cttttgatgg tagagttcca gtgattc                                 27

<210> SEQ ID NO 45
<211> LENGTH: 24
<212> TYPE: DNA
<213> ORGANISM: Artificial Sequence
<220> FEATURE:
<223> OTHER INFORMATION: PCR primer-probe

<400> SEQUENCE: 45
cagcattgtc tgtcctccct ggca                                    24

<210> SEQ ID NO 46
<211> LENGTH: 20
<212> TYPE: DNA
<213> ORGANISM: Artificial Sequence
<220> FEATURE:
<223> OTHER INFORMATION: PCR primer-probe

<400> SEQUENCE: 46
gcatcaggct gtcattatgg                                         20

<210> SEQ ID NO 47
<211> LENGTH: 20
<212> TYPE: DNA
<213> ORGANISM: Artificial Sequence
<220> FEATURE:
<223> OTHER INFORMATION: PCR primer-probe

<400> SEQUENCE: 47
agtagttgtg ctgcccttcc                                         20

<210> SEQ ID NO 48
<211> LENGTH: 28
<212> TYPE: DNA
<213> ORGANISM: Artificial Sequence
<220> FEATURE:
<223> OTHER INFORMATION: PCR primer-probe

<400> SEQUENCE: 48
tgtccttacc tgtgggagct gtaaggtc                                28

<210> SEQ ID NO 49
<211> LENGTH: 24
<212> TYPE: DNA
<213> ORGANISM: Artificial Sequence
<220> FEATURE:
<223> OTHER INFORMATION: PCR primer-probe

<400> SEQUENCE: 49
ccattctatc atcaacgggt acaa                                    24

```
<210> SEQ ID NO 50
<211> LENGTH: 23
<212> TYPE: DNA
<213> ORGANISM: Artificial Sequence
<220> FEATURE:
<223> OTHER INFORMATION: PCR primer-probe

<400> SEQUENCE: 50
tcagcaagtg ggaaggtgta atc                                               23

<210> SEQ ID NO 51
<211> LENGTH: 25
<212> TYPE: DNA
<213> ORGANISM: Artificial Sequence
<220> FEATURE:
<223> OTHER INFORMATION: PCR primer-probe

<400> SEQUENCE: 51
tctccacaga caaggccagg actcg                                             25

<210> SEQ ID NO 52
<211> LENGTH: 20
<212> TYPE: DNA
<213> ORGANISM: Artificial Sequence
<220> FEATURE:
<223> OTHER INFORMATION: PCR primer-probe

<400> SEQUENCE: 52
catcttccag gaggaccact                                                   20

<210> SEQ ID NO 53
<211> LENGTH: 20
<212> TYPE: DNA
<213> ORGANISM: Artificial Sequence
<220> FEATURE:
<223> OTHER INFORMATION: PCR primer-probe

<400> SEQUENCE: 53
tccgaccttc aatcatttca                                                   20

<210> SEQ ID NO 54
<211> LENGTH: 24
<212> TYPE: DNA
<213> ORGANISM: Artificial Sequence
<220> FEATURE:
<223> OTHER INFORMATION: PCR primer-probe

<400> SEQUENCE: 54
ctctgtggca ccctggacta cctg                                              24

<210> SEQ ID NO 55
<211> LENGTH: 20
<212> TYPE: DNA
<213> ORGANISM: Artificial Sequence
<220> FEATURE:
<223> OTHER INFORMATION: PCR primer-probe

<400> SEQUENCE: 55
cctggaggct gcaacatacc                                                   20

<210> SEQ ID NO 56
<211> LENGTH: 23
<212> TYPE: DNA
<213> ORGANISM: Artificial Sequence
<220> FEATURE:
<223> OTHER INFORMATION: PCR primer-probe
```

```
<400> SEQUENCE: 56
tacaatggct ttggaggata gca                                          23

<210> SEQ ID NO 57
<211> LENGTH: 25
<212> TYPE: DNA
<213> ORGANISM: Artificial Sequence
<220> FEATURE:
<223> OTHER INFORMATION: PCR primer-probe

<400> SEQUENCE: 57
atcctcctga agccctttc gcagc                                         25

<210> SEQ ID NO 58
<211> LENGTH: 20
<212> TYPE: DNA
<213> ORGANISM: Artificial Sequence
<220> FEATURE:
<223> OTHER INFORMATION: PCR primer-probe

<400> SEQUENCE: 58
tgttttgatt cccgggctta                                              20

<210> SEQ ID NO 59
<211> LENGTH: 24
<212> TYPE: DNA
<213> ORGANISM: Artificial Sequence
<220> FEATURE:
<223> OTHER INFORMATION: PCR primer-probe

<400> SEQUENCE: 59
caaagctgtc agctctagca aaag                                         24

<210> SEQ ID NO 60
<211> LENGTH: 28
<212> TYPE: DNA
<213> ORGANISM: Artificial Sequence
<220> FEATURE:
<223> OTHER INFORMATION: PCR primer-probe

<400> SEQUENCE: 60
tgccttcttc ctccctcact tctcacct                                     28

<210> SEQ ID NO 61
<211> LENGTH: 20
<212> TYPE: DNA
<213> ORGANISM: Artificial Sequence
<220> FEATURE:
<223> OTHER INFORMATION: PCR primer-probe

<400> SEQUENCE: 61
gccaactgct ttcatttgtg                                              20

<210> SEQ ID NO 62
<211> LENGTH: 20
<212> TYPE: DNA
<213> ORGANISM: Artificial Sequence
<220> FEATURE:
<223> OTHER INFORMATION: PCR primer-probe

<400> SEQUENCE: 62
actcaggccc atttcctta                                               20
```

```
<210> SEQ ID NO 63
<211> LENGTH: 28
<212> TYPE: DNA
<213> ORGANISM: Artificial Sequence
<220> FEATURE:
<223> OTHER INFORMATION: PCR primer-probe

<400> SEQUENCE: 63
agggatctga accaatacag agcagaca                                              28

<210> SEQ ID NO 64
<211> LENGTH: 66
<212> TYPE: DNA
<213> ORGANISM: Artificial Sequence
<220> FEATURE:
<223> OTHER INFORMATION: PCR Amplicon

<400> SEQUENCE: 64
cagcagatgt ggatcagcaa gcaggagtat gacgagtccg gcccctccat cgtccaccgc           60
aaatgc                                                                     66

<210> SEQ ID NO 65
<211> LENGTH: 81
<212> TYPE: DNA
<213> ORGANISM: Artificial Sequence
<220> FEATURE:
<223> OTHER INFORMATION: PCR Amplicon

<400> SEQUENCE: 65
cgttgtcagc acttggaata caagatggtt gccgggtcat gttaattggg aaaagaaca           60 gtccacagga agaggttgaa c                                                    81

<210> SEQ ID NO 66
<211> LENGTH: 73
<212> TYPE: DNA
<213> ORGANISM: Artificial Sequence
<220> FEATURE:
<223> OTHER INFORMATION: PCR Amplicon

<400> SEQUENCE: 66
cagatggacc tagtacccac tgagatttcc acgccgaagg acagcgatgg gaaaaatgcc          60
cttaaatcat agg                                                             73

<210> SEQ ID NO 67
<211> LENGTH: 84
<212> TYPE: DNA
<213> ORGANISM: Artificial Sequence
<220> FEATURE:
<223> OTHER INFORMATION: PCR Amplicon

<400> SEQUENCE: 67
ttcaggttgt tgcaggagac catgtacatg actgtctcca ttattgatcg gttcatgcag          60
aataattgtg tgcccaagaa gatg                                                 84

<210> SEQ ID NO 68
<211> LENGTH: 74
<212> TYPE: DNA
<213> ORGANISM: Artificial Sequence
<220> FEATURE:
<223> OTHER INFORMATION: PCR Amplicon

<400> SEQUENCE: 68
tggttcccag ccctgtgtcc acctccaagc ccagattcag attcgagtca tgtacacaac          60
ccagggtgga ggag                                                            74
```

```
<210> SEQ ID NO 69
<211> LENGTH: 77
<212> TYPE: DNA
<213> ORGANISM: Artificial Sequence
<220> FEATURE:
<223> OTHER INFORMATION: PCR Amplicon

<400> SEQUENCE: 69
tgacaatcag cacacctgca ttcaccgctc ggaagagggc ctgagctgca tgaataagga    60
tcacggctgt agtcaca                                                   77

<210> SEQ ID NO 70
<211> LENGTH: 67
<212> TYPE: DNA
<213> ORGANISM: Artificial Sequence
<220> FEATURE:
<223> OTHER INFORMATION: PCR Amplicon

<400> SEQUENCE: 70
tgtctcactg agcgagcaga atctggtgga ctgttcgcgt cctcaaggca atcagggctg    60
caatggt                                                              67

<210> SEQ ID NO 71
<211> LENGTH: 68
<212> TYPE: DNA
<213> ORGANISM: Artificial Sequence
<220> FEATURE:
<223> OTHER INFORMATION: PCR Amplicon

<400> SEQUENCE: 71
cgtggtgccc ctctatgacc tgctgctgga gatgctggac gcccaccgcc tacatgcgcc    60
cactagcc                                                             68

<210> SEQ ID NO 72
<211> LENGTH: 74
<212> TYPE: DNA
<213> ORGANISM: Artificial Sequence
<220> FEATURE:
<223> OTHER INFORMATION: PCR Amplicon

<400> SEQUENCE: 72
attccaccca tggcaaattc catggcaccg tcaaggctga aacgggaag cttgtcatca     60 atggaaatcc catc                                                      74

<210> SEQ ID NO 73
<211> LENGTH: 67
<212> TYPE: DNA
<213> ORGANISM: Artificial Sequence
<220> FEATURE:
<223> OTHER INFORMATION: PCR Amplicon

<400> SEQUENCE: 73
ccatctgcat ccatcttgtt tgggctcccc acccttgaga agtgcctcag ataatacct     60 ggtggcc                                                              67

<210> SEQ ID NO 74
<211> LENGTH: 86
<212> TYPE: DNA
<213> ORGANISM: Artificial Sequence
<220> FEATURE:
<223> OTHER INFORMATION: PCR Amplicon
```

-continued

<400> SEQUENCE: 74
aagctatgag gaaaagaagt acacgatggg ggacgctcct gattatgaca gaagccagtg        60
gctgaatgaa aaattcaagc tgggcc                                              86

<210> SEQ ID NO 75
<211> LENGTH: 73
<212> TYPE: DNA
<213> ORGANISM: Artificial Sequence
<220> FEATURE:
<223> OTHER INFORMATION: PCR Amplicon

<400> SEQUENCE: 75
cccactcagt agccaagtca caatgtttgg aaaacagccc gtttacttga gcaagactga        60
taccacctgc gtg                                                            73

<210> SEQ ID NO 76
<211> LENGTH: 70
<212> TYPE: DNA
<213> ORGANISM: Artificial Sequence
<220> FEATURE:
<223> OTHER INFORMATION: PCR Amplicon

<400> SEQUENCE: 76
cggtgtgaga agtgcagcaa gccctgtgcc cgagtgtgct atggtctggg catggagcac        60
ttgcgagagg                                                                70

<210> SEQ ID NO 77
<211> LENGTH: 80
<212> TYPE: DNA
<213> ORGANISM: Artificial Sequence
<220> FEATURE:
<223> OTHER INFORMATION: PCR Amplicon

<400> SEQUENCE: 77
cggactttgg gtgcgacttg acgagcggtg gttcgacaag tggccttgcg ggccggatcg        60
tcccagtgga agagttgtaa                                                     80

<210> SEQ ID NO 78
<211> LENGTH: 74
<212> TYPE: DNA
<213> ORGANISM: Artificial Sequence
<220> FEATURE:
<223> OTHER INFORMATION: PCR Amplicon

<400> SEQUENCE: 78
gccgagatcg ccaagatgtt gccagggagg acagacaatg ctgtgaagaa tcactggaac        60
tctaccatca aaag                                                           74

<210> SEQ ID NO 79
<211> LENGTH: 85
<212> TYPE: DNA
<213> ORGANISM: Artificial Sequence
<220> FEATURE:
<223> OTHER INFORMATION: PCR Amplicon

<400> SEQUENCE: 79
gcatcaggct gtcattatgg tgtccttacc tgtgggagct gtaaggtctt ctttaagagg        60
gcaatggaag ggcagcacaa ctact                                               85

```
<210> SEQ ID NO 80
<211> LENGTH: 75
<212> TYPE: DNA
<213> ORGANISM: Artificial Sequence
<220> FEATURE:
<223> OTHER INFORMATION: PCR Amplicon

<400> SEQUENCE: 80
ccattctatc atcaacgggt acaaacgagt cctggccttg tctgtggaga cggattacac    60
cttcccactt gctga                                                    75

<210> SEQ ID NO 81
<211> LENGTH: 69
<212> TYPE: DNA
<213> ORGANISM: Artificial Sequence
<220> FEATURE:
<223> OTHER INFORMATION: PCR Amplicon

<400> SEQUENCE: 81
catcttccag gaggaccact ctctgtggca ccctggacta cctgccccct gaaatgattg    60
aaggtcgga                                                           69

<210> SEQ ID NO 82
<211> LENGTH: 90
<212> TYPE: DNA
<213> ORGANISM: Artificial Sequence
<220> FEATURE:
<223> OTHER INFORMATION: PCR Amplicon

<400> SEQUENCE: 82
cctggaggct gcaacatacc tcaatcctgt cccaggccgg atcctcctga agcccttttc    60
gcagcactgc tatcctccaa agccattgta                                    90

<210> SEQ ID NO 83
<211> LENGTH: 80
<212> TYPE: DNA
<213> ORGANISM: Artificial Sequence
<220> FEATURE:
<223> OTHER INFORMATION: PCR Amplicon

<400> SEQUENCE: 83
tgttttgatt cccgggctta ccaggtgaga agtgagggag gaagaaggca gtgtcccttt    60
tgctagagct gacagctttg                                               80

<210> SEQ ID NO 84
<211> LENGTH: 68
<212> TYPE: DNA
<213> ORGANISM: Artificial Sequence
<220> FEATURE:
<223> OTHER INFORMATION: PCR Amplicon

<400> SEQUENCE: 84
gccaactgct ttcatttgtg agggatctga accaatacag agcagacata aaggaaatgg    60
gcctgagt                                                            68
```

EXPRESSION PROFILE ALGORITHM AND TEST FOR CANCER PROGNOSIS

The present application is a continuation of U.S. application Ser. No. 10/883,303, filed Jun. 30, 2004, now U.S. Pat. No. 7,526,387 which application claims the benefit under 35 U.S.C. 119(e) of the filing date of U.S. application Ser. Nos. 60/486,302, filed on Jul. 10, 2003 and 60/526,947 filed on Dec. 3, 2003.

BACKGROUND OF THE INVENTION

1. Field of the Invention

The present invention provides a noninvasive, quantitative test for prognosis determination in cancer patients. The test relies on measurements of the tumor levels of certain messenger RNAs (mRNAs) or the corresponding gene expression products. These mRNA or protein levels are entered into a polynomial formula (algorithm) that yields a numerical score, which indicates recurrence risk (recurrence score) or the likelihood of patient response to therapy (response score).

2. Description of the Related Art

A need exists for clinical tests that help oncologists make well reasoned treatment decisions. One of the most fundamental decisions an oncologist faces in everyday practice is whether to treat or forego treatment of a particular patient with chemotherapeutic agents. Current therapeutic agents for cancer generally have modest efficacy accompanied by substantial toxicity. Thus, it is highly desirable to predetermine which patients (post-resection of the primary tumor) are likely to have metastatic recurrence. If there were a reliable way to obtain this information, high risk patients could be selected for adjuvant chemotherapy and patients unlikely to have cancer recurrence could be spared unnecessary exposure to the adverse events associated with chemotherapy. Similarly, before subjecting a patient (either before or after resection of a primary tumor) to a particular treatment, it would be desirable to know whether the patient is likely to respond to such treatment. For patients unlikely to respond to a certain treatment modality (e.g. treatment with certain chemotherapeutic agents and/or radiology), other treatments can be designed and used, without wasting valuable time.

Although modern molecular biology and biochemistry have revealed hundreds of genes whose activities influence the behavior and state of differentiation of tumor cells, and their sensitivity or resistance to certain therapeutic drugs, with a few exceptions, the status of these genes has not been exploited for the purpose of routinely making clinical decisions about drug treatments. One notable exception is the use of estrogen receptor (ER) protein expression in breast carcinomas to select patients for treatment with anti-estrogen drugs, such as tamoxifen. Another exceptional example is the use of ErbB2 (Her2) protein expression in breast carcinomas to select patients for treatment with the anti-Her2 antibody, Herceptin® (Genentech, Inc., South San Francisco, Calif.).

The present invention pertains to cancer, such as breast cancer, the biological understanding of which is still rudimentary. It is clear that the classification of breast cancer into a few subgroups, such as ErbB2+ subgroup, and subgroups characterized by low to absent gene expression of the estrogen receptor (ER) and a few additional factors (Perou et al., *Nature* 406:747-752 (2000) does not reflect the cellular and molecular heterogeneity of breast cancer, and does not permit optimization of patient treatment and care. The same is true for other types of cancers, many of which are much less studied and understood than breast cancer.

Currently, diagnostic tests used in clinical practice are single analyte, and therefore fail to capture the potential value of knowing relationships between dozens of different tumor markers. Moreover, diagnostic tests are frequently not quantitative, relying on immunohistochemistry. This method often yields different results in different laboratories, in part because the reagents are not standardized, and in part because the interpretations are subjective and cannot be easily quantified. RNA-based tests have not often been used because of the problem of RNA degradation over time and the fact that it is difficult to obtain fresh tissue samples from patients for analysis. Fixed paraffin-embedded tissue is more readily available and methods have been established to detect RNA in fixed tissue. However, these methods typically do not allow for the study of large numbers of genes from small amounts of material. Thus, traditionally, fixed tissue has been rarely used other than for immunohistochemistry detection of proteins.

In the past few years, several groups have published studies concerning the classification of various cancer types by microarray gene expression analysis {see, e.g. Golub et al., *Science* 286:531-537 (1999); Bhattacharjae et al., *Proc. Natl. Acad. Sci. USA* 98:13790-13795 (2001); Chen-Hsiang et al., *Bioinformatics* 17 (Suppl. 1):S316-S322 (2001); Ramaswamy et al. *Proc. Natl. Acad. Sci. USA* 98:15149-15154 (2001)). Certain classifications of human breast cancers based on gene expression patterns have also been reported {Martin et al., *Cancer Res.* 60:2232-2238 (2000); West et al., *Proc. Natl. Acad. Sci. USA* 98:11462-11467 (2001)}. Most of these studies focus on improving and refining the already established classification of various types of cancer, including breast cancer. A few studies identify gene expression patterns that may be prognostic {Sorlie et al., *Proc. Natl. Acad. Sci. USA* 98:10869-10874 (2001); Yan et al., *Cancer Res.* 61:8375-8380 (2001); Van De Vivjer et al. *New England Journal of Medicine* 347: 1999-2009 (2002)}, but due to inadequate numbers of screened patients, are not yet sufficiently validated to be widely used clinically.

SUMMARY OF THE INVENTION

This invention provides an algorithm-based prognostic test for determining the likelihood of cancer recurrence and/or the likelihood that a patient responds well to a treatment modality. In a particular aspect, the invention provides an algorithm and prognostic test for determining the likelihood of breast cancer recurrence and/or patient response to treatment, in patients with invasive breast cancer. Hence, the invention finds utility in making treatment decisions concerning the therapy of cancer patients, such as, for example, lymph node-negative breast cancer patients who have undergone surgical resection of their tumors. Specifically, the algorithm and related prognostic test helps guide the decision whether to treat such patients with adjunct chemotherapy, and if the answer is affirmative, which treatment option(s) to choose.

Features of the algorithm that distinguish it from other breast cancer prognostic methods include: 1) a unique set of test mRNAs (or the corresponding gene expression products) used to determine recurrence likelihood, 2) certain weights used to combine the expression data into a formula, 3) thresholds used to divide patients into groups of different levels of risk, such as low, medium, and high risk groups. The algorithm yields a numerical recurrence score (RS) or, if patient response to treatment is assessed, response to therapy score (RTS). The test requires a laboratory assay to measure the levels of the specified mRNAs or their expression products, but can utilize very small amounts of either fresh tissue, or frozen tissue or fixed, paraffin-embedded tumor biopsy specimens that have already been necessarily collected from patients and archived. Thus, the test can be noninvasive. It is also compatible with several different methods of tumor tissue harvest, for example, via core biopsy or fine needle aspiration. The tumor tissue can be, but does not have to be, grossly dissected away from normal tissue. Further, for each member of the gene set, the invention specifies oligonucleotide sequences that can be used in the test. The mRNA levels are normalized against a specified set of reference genes. The invention encompasses all subsequences of the test and reference genes, including 5' and 3' untranslated and intron sequences. Protein levels can be normalized in an analogous manner.

Thus, in one aspect, the invention concerns a method of classifying a tumor according to the likelihood of cancer recurrence or response to therapy in a mammalian subject, comprising (a) subjecting a biological sample comprising cancer cells obtained from said subject to gene or protein expression profiling;

(b) quantifying the gene or protein expression level of multiple individual genes so as to determine an expression value for each gene;

(c) creating subsets of the gene or protein expression values, each subset comprising expression values for genes or proteins linked by a cancer-related biological function and/or by co-expression;

(d) multiplying the expression level of each gene within a subset by a coefficient reflecting its relative contribution to cancer recurrence or response to therapy within said subset and adding the products of multiplication to yield a term for said subset;

(e) multiplying the term of each subset by a factor reflecting its contribution to cancer recurrence or response to therapy; and (f) producing the sum of terms for each subset multiplied by said factor to produce a recurrence score (RS) or a response to therapy (RTS) score, wherein the contribution of each subset which does not show a linear correlation with cancer recurrence or response to therapy is included only above a predetermined threshold level, and wherein the subsets in which increased expression of the genes or proteins included reduce risk of cancer recurrence are assigned a negative value, and the subsets increased expression of the genes or proteins included increase risk of cancer recurrence are assigned a positive value.

The algorithm is suitable to assess the risk of cancer recurrence or response to therapy for any type of cancer, but is exemplified, without limitation, for breast cancer.

In the case of breast cancer, the genes contributing to the recurrence algorithm include 16 test genes and 5 reference genes.

The test genes/mRNAs specified are: Grb7; Her2; ER; PR; BCl2; CEGP1; SURV; Ki-67; MYBL2; CCNB1; STK15; CTSL2; STMY3; GSTM1; BAG1; CD68.

The reference genes/mRNAs are: β-ACTIN; GAPDH; RPLPO; TFRC; GUS.

For breast cancer. the above set of 16 test genes includes 4 multi-gene subsets. The gene members of these subsets have in common both correlated expression and categories of biological function: a proliferation subset comprising SURV, Ki-67, MYBL2, CCNB1 and STK15; a growth factor subset comprising Her2 and Grb7; an estrogen receptor subset comprising ER, PR, Bcl2, and CEGP1; an invasion subset comprising genes for the invasive proteases CTSL2 and STMY3.

Thus, in a particular aspect, the invention concerns a method for determining the likelihood of breast cancer recurrence or response to hormonal therapy in a mammalian subject comprising:

(a) determining the expression levels of the RNA transcripts of GRB7, HER2, ER, PR, Bcl2, CEGP1, SURV, Ki.67, MYBL2, CCNB1, STK15, CTSL2, and STMY3, or their expression products, or corresponding substitute genes or their expression products, in a biological sample containing tumor cells obtained from said subject;

(b) creating the following gene subsets:
 (i) growth factor subset: GRB7 and HER2;
 (ii) differentiation (estrogen receptor) subset: ER, PR, Bcl2, and CEGP1;
 (iii) proliferation subset: SURV, Ki.67, MYBL2, CCNB1, and STK15; and
 (iv) invasion subset: CTSL2, and STMY3;
 wherein a gene within any of subsets (i)-(iv) can be substituted by substitute gene which coexpresses with said gene in said tumor with a Pearson correlation coefficient of $\geq 0.40$; and (c) calculating the recurrence score (RS) or response to therapy score (RTS) for said subject by weighting the contributions of each of subsets (i)-(iv), to breast cancer recurrence or response to therapy.

In a particular embodiment, the method further comprises determining the expression levels of RNA transcripts of CD68, GSTM1 and BAG1 or their expression products, or corresponding substitute genes or their expression products, and including the contribution of said genes or substitute genes to breast cancer recurrence or response to therapy in calculating the RS or RTS, wherein a higher RS or RTS represents an increased likelihood of breast cancer recurrence or lower likelihood of response to therapy, as applicable.

In a specific aspect, the invention concerns a method for determining the likelihood of breast cancer recurrence in a mammalian subject comprising:

(a) determining the expression levels of GRB7, HER2, EstR1, PR, Bcl2, CEGP1, SURV, Ki.67, MYBL2, CCNB1, STK15, CTSL2, STMY3, CD68, GSTM1, and BAG1, or their expression products, in a biological sample containing tumor cells obtained from said subject; and (b) calculating the recurrence score (RS) by the following equation:

$$RS = (0.23 \text{ to } 0.70) \times GRB7\text{axisthresh} - (0.17 \text{ to } 0.51) \times ERaxis + (0.53 \text{ to } 1.56) \times \text{prolifaxisthresh} + (0.07 \text{ to } 0.21) \times \text{invasionaxis} + (0.03 \text{ to } 0.15) \times CD68 - (0.04 \text{ to } 0.25) \times GSTM1 - (0.05 \text{ to } 0.22) \times BAG1$$

wherein
(i) GRB7 axis=$(0.45 \text{ to } 1.35) \times GRB7 + (0.05 \text{ to } 0.15) \times HER2$;
(ii) if GRB7 axis<-2, then GRB7 axis thresh=-2, and if GRB7 axis$\geq -2$, then GRB7 axis thresh=GRB7 axis;
(iii) ER axis=$(Est1+PR+Bcl2+CEGP1)/4$;
(iv) prolifaxis=$(SURV+Ki.67+MYBL2+CCNB1+STK15)/5$;
(v) if prolifaxis<-3.5, then prolifaxisthresh=-3.5, if prolifaxis$\geq -3.5$, then prolifaxishresh=prolifaxis; and
(vi) invasionaxis=$(CTSL2+STMY3)/2$, wherein the terms for all individual genes for which ranges are not specifically shown can vary between about 0.5 and 1.5, and wherein a higher RS represents an increased likelihood of breast cancer recurrence.

The laboratory assay for gene expression can use a variety of different platforms. The preferred embodiment for use with fixed paraffin-embedded tissues is quantitative reverse transcriptase polymerase chain reaction qRT-PCR. However, the other technology platforms including mass spectroscopy and DNA microarrays, and can also be used. In the case of DNA microarrays the polynucleotide probes can be cDNAs ("cDNA arrays") that are typically about 500 to 5000 bases long, although shorter or longer cDNAs can also be used and are within the scope of this invention. Alternatively, the polynucleotides can be oligonucleotides (DNA microarrays), which are typically about 20 to 80 bases long, although shorter and longer oligonucleotides are also suitable and are within the scope of the invention. The solid surface can, for example, be glass or nylon, or any other solid surface typically used in preparing arrays, such as microarrays, and is typically glass.

BRIEF DESCRIPTION OF THE DRAWINGS

Table 1 lists test and reference genes, expression of which is used to construct the breast cancer recurrence algorithm. The table includes accession numbers for the genes, sequences for the forward and reverse primers (designated by "f" and "r", respectively) and probes (designated by "p") used for PCR amplification.

Table 2 shows the amplicon sequences of the aforementioned genes.

DETAILED DESCRIPTION OF THE PREFERRED EMBODIMENT

A. Definitions

Figure 1A:
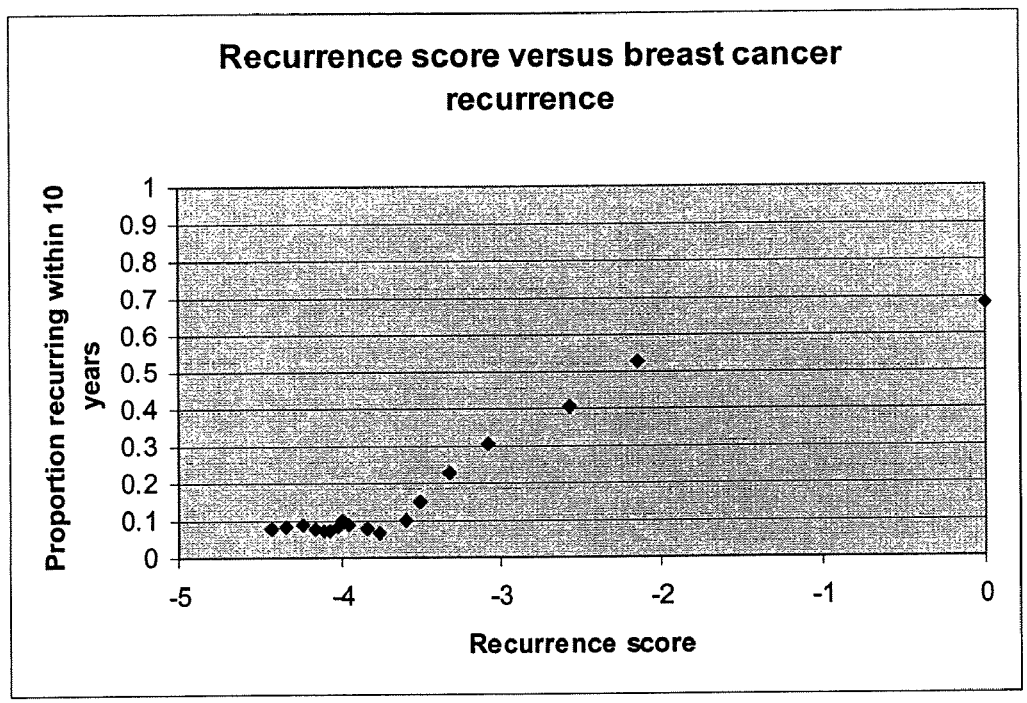
FIGS. 1A and B present results from a clinical study of 242 patients with invasive, lymph node-negative breast cancer, for whom 10 year recurrence data were available. The FIG. 1A presents proportion of patients with actual cancer recurrence (Kaplan-Meier method) versus calculated recurrence scores. Patients are grouped in 5 percentile units, except for patients with scores<-4.5, who are all grouped together.

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "microarray" refers to an ordered arrangement of hybridizable array elements, preferably polynucleotide probes, on a substrate.

The term "polynucleotide," when used in singular or plural, generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The terms "differentially expressed gene," "differential gene expression" and their synonyms, which are used interchangeably, refer to a gene whose expression is activated to a higher or lower level in a subject suffering from a disease, specifically cancer, such as breast cancer, relative to its expression in a normal or control subject. The terms also include genes whose expression is activated to a higher or lower level at different stages of the same disease. It is also understood that a differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes or their gene products, or a comparison of the ratios of the expression between two or more genes or their gene products, or even a comparison of two differently processed products of the same gene, which differ between normal subjects and subjects suffering from a disease, specifically cancer, or between various stages of the same disease. Differential expression includes both quantitative, as well as qualitative, differences in the temporal or cellular expression pattern in a gene or its expression products among, for example, normal and diseased cells, or among cells which have undergone different disease events or disease stages. For the purpose of this invention, "differential gene expression" is considered to be present when there is at least an about two-fold, preferably at least about four-fold, more preferably at least about six-fold, most preferably at least about ten-fold difference between the expression of a given gene in normal and diseased subjects, or in various stages of disease development in a diseased subject.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in proportion to the number of copies made of the particular gene expressed.

The term "prognosis" is used herein to refer to the prediction of the likelihood of cancer-attributable death or progression, including recurrence, metastatic spread, and drug resistance, of a neoplastic disease, such as breast cancer.

The term "prediction" is used herein to refer to the likelihood that a patient will respond either favorably or unfavorably to a drug or set of drugs, and also the extent of those responses, or that a patient will survive, following surgical removal or the primary tumor and/or chemotherapy for a certain period of time without cancer recurrence. The predictive methods of the present invention are valuable tools in predicting if a patient is likely to respond favorably to a treatment regimen, such as surgical intervention, chemotherapy with a given drug or drug combination, and/or radiation therapy, or whether long-term survival of the patient, following surgery and/or termination of chemotherapy or other treatment modalities is likely.

The term "long-term" survival is used herein to refer to survival for at least years, more preferably for at least 8 years, most preferably for at least 10 years following surgery or other treatment.

The term "tumor," as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, and brain cancer.

The "pathology" of (tumor) cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

"Moderately stringent conditions" may be identified as described by Sambrook et al., Molecular Cloning: A Laboratory Manual, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

In the context of the present invention, reference to "at least one," "at least two," "at least five," etc. of the genes listed in any particular gene set means any one or any and all combinations of the genes listed.

The term "(lymph) node negative" cancer, such as "(lymph) node negative" breast cancer, is used herein to refer to cancer that has not spread to the lymph nodes.

The term "gene expression profiling" is used in the broadest sense, and includes methods of quantification of mRNA and/or protein levels in a biological sample.

The term "adjuvant therapy" is generally used to treatment that is given in addition to a primary (initial) treatment. In cancer treatment, the term "adjuvant therapy" is used to refer to chemotherapy, hormonal therapy and/or radiation therapy following surgical removal of tumor, with the primary goal of reducing the risk of cancer recurrence.

"Neoadjuvant therapy" is adjunctive or adjuvant therapy given prior to the primary (main) therapy. Neoadjuvant therapy includes, for example, chemotherapy, radiation therapy, and hormone therapy. Thus, chemotherapy may be administered prior to surgery to shrink the tumor, so that surgery can be more effective, or, in the case of previously unoperable tumors, possible.

The term "cancer-related biological function" is used herein to refer to a molecular activity that impacts cancer success against the host, including, without limitation, activities regulating cell proliferation, programmed cell death (apoptosis), differentiation, invasion, metastasis, tumor suppression, susceptibility to immune surveillance, angiogenesis, maintenance or acquisition of immortality.

B. Detailed Description

The practice of the present invention will employ, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", $2^{nd}$ edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", $4^{th}$ edition (D. M. Weir & C. C. Blackwell, eds., Blackwell Science Inc., 1987); "Gene Transfer Vectors for Mammalian Cells" (J. M. Miller & M. P. Calos, eds., 1987); "Current Protocols in Molecular Biology" (F. M. Ausubel et al., eds., 1987); and "PCR: The Polymerase Chain Reaction", (Mullis et al., eds., 1994).

The present invention provides an algorithm for determining the likelihood of cancer recurrence or response to therapy in cancer patients. The method is based on (1) the identification and clustering of a set of genes that can serve as markers of cancer recurrence or the likelihood of patient response to a particular therapy, (2) certain weights assigned to the clusters and the individual genes within the clusters that reflect their value in predicting cancer recurrence or response to therapy and used to combine the expression data into a formula; and (3) determination of threshold values used to divide patients into groups with varying degrees of risk of cancer recurrence, or with varying likelihood of response to treatment, such as low, medium, and high risk groups or groups in which the likelihood of patient response to a particular treatment is low, medium or high. The algorithm yields a numerical recurrence score (RS) or response to treatment score (RTS), which can be used to make treatment decisions concerning the therapy of cancer patients. The first step in generating data to be analyzed by the algorithm of the present invention is gene or protein expression profiling.

1. Techniques of Expression Profiling

The present invention requires an assay to measure the levels of specified genes (mRNAs) or their expression products (proteins) in a biological sample comprising cancer cells. Typically, the biological sample is a fresh or archived tissue sample obtained from a tumor, e.g. by tumor biopsy or aspiration, but biological fluids containing tumor cells can also be used in the analysis.

In its most common form, gene expression profiling involves the determination of mRNA levels in a tissue sample, such as a fixed, paraffin-embedded tumor biopsy specimen that has already been collected from the patient and archived. Thus, the test can be completely non-invasive. It is also compatible with several different methods of tumor tissue harvest, for example, core biopsy and fine needle aspiration. The tumor tissue can be, but does not need to be, grossly dissected away from normal tissue.

Methods of gene expression profiling directed to measuring mRNA levels can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, *Biotechniques* 13:852-854 (1992)); and reverse transcription polymerase chain reaction (RT-PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

In all of these techniques, the first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andrés et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include Master-Pure™ Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

While the practice of the invention will be illustrated with reference to techniques developed to determine mRNA levels in a biological (e.g. tissue) sample, other techniques, such as methods of proteomics analysis are also included within the broad concept of gene expression profiling, and are within the scope herein. In general, a preferred gene expression profiling method for use with paraffin-embedded tissue is quantitative reverse transcriptase polymerase chain reaction (qRT-PCR), however, other technology platforms, including mass spectroscopy and DNA microarrays can also be used.

In the following sections, a series of representative, but not exhaustive, gene expression profiling techniques will be discussed in greater detail.

2. Reverse Transcriptase PCR (RT-PCR)

Of the techniques listed above, the most sensitive and most flexible quantitative method is qRT-PCR, which can be used to compare mRNA levels in different sample populations, in normal and tumor tissues, with or without drug treatment, to characterize patterns of gene expression, to discriminate between closely related mRNAs, and to analyze RNA structure.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Research 6:986-994 (1996).

3. Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., Proc. Natl. Acad. Sci. USA 93(2):106-149 (1996)). Microarray analysis can be performed by commercially available equipment, following manufacturer's protocols, such as by using the Affymetrix GenChip technology, or Incyte's microarray technology.

The development of microarray methods for large-scale analysis of gene expression makes it possible to search systematically for molecular markers of cancer classification and outcome prediction in a variety of tumor types.

4. Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

5. Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 μm diameter microbeads. First, a microbead library of DNA templates is constructed by in vitro cloning. This is followed by the assembly of a planar array of the template-containing microbeads in a flow cell at a high density (typically greater than $3 \times 10^6$ microbeads/$cm^2$). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

6. Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

7. Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

8. Cancer Gene Set, Assayed Gene Subsequences and Clinical Application of Gene Expression Data An important aspect of the present invention is to use the measured expression of certain genes, or their expression products, by cancer, e.g. breast cancer, tissue to provide prognostic information. For this purpose, it is necessary to correct for (normalize away) both differences in the amount of RNA assayed and variability in the quality of the RNA used. Therefore, the assay typically measures and incorporates the expression of certain normalizing genes, including well know housekeeping genes, such as GAPDH and β-ACTIN. Alternatively, normalization can be based on the mean or median signal (Ct) of all of the assayed genes or a large subset thereof (global normalization approach). Throughout the disclosure, unless noted otherwise, reference to expression levels of a gene assumes normalized expression relative to the reference set although this is not always explicitly stated.

9. Algorithm to Generate a Cancer Recurrence Score

When qRT-PCR is used to measure mRNA levels, mRNA amounts are expressed in Ct (threshold cycle) units (Held et al., *Genome Research* 6:986-994 (1996)). The averaged sum of reference mRNA Cts is set as zero, and each measured test mRNA Ct is given relative to this zero point. For example, if, for a certain patient tumor specimen the average of Cts of the 5 reference genes found to be 31 and Ct of the test gene CRB7 is found to be 35, the reported value for GRB7 is −4 (i.e. 31-35).

As a first step following the quantitative determination of mRNA levels, the genes identified in the tumor specimen and known to be associated with the molecular pathology of cancer are grouped into subsets. Thus, genes known to be associated with proliferation will constitute the "proliferation subset" (axis). Genes known to be associated with invasion of cancer will constitute the "invasion subset" (axis). Genes associated with key growth factor receptor pathway(s) will constitute the "growth factor subset" (axis). Genes known to be involved with activating or signaling through the estrogen receptor (ER) will constitute the "estrogen receptor subset" (axis). This list of subsets is, of course, not limiting. The subsets (axes) created will depend on the particular cancer, i.e. breast, prostate, pancreatic, lung, etc. cancer. In general, genes the expression of which is known to correlate with each other, or which are known to be involved in the same pathway are grouped in the same axis.

In the next step, the measured tumor level of each mRNA in a subset is multiplied by a coefficient reflecting its relative intra-set contribution to the risk of cancer recurrence and this product is added to the other products between mRNA levels in the subset and their coefficients, to yield a term, e.g. a proliferation term, an invasion term, a growth factor term, etc. For example, in the case of lymph node-negative invasive breast cancer the growth factor term is (0.45 to 1.35)×GRB7+ (0.05 to 0.15)×Her2 (see the Example below).

The contribution of each term to the overall recurrence score is weighted by use of a coefficient. For example, in the case of lymph node-negative invasive breast cancer the coefficient of the growth factor term can be between 0.23 and 0.70.

Additionally, for some terms, such as the growth factor and proliferation terms, a further step is performed. If the relationship between the term and the risk of recurrence is non-linear, a non-linear functional transform of the term, such as a threshold is used Thus, in lymph node-negative invasive breast cancer, when the growth factor term is found at <−2 the value is fixed at −2. When the proliferation term is found at <−3.5 the value is fixed at −3.5.

The sum of the terms obtained provides the recurrence score (RS).

A relationship between recurrence score (RS) and risk of recurrence has been found by measuring expression of the test and reference genes in biopsied tumor specimens from a population of lymph node-negative patients with invasive breast cancer and applying the algorithm.

It is noted that the RS scale generated by the algorithm of the present invention can be adjusted in various ways. Thus, while the RS scale specifically described above effectively runs from −4.5 to −2.0, the range could be selected such that the scale run from 0 to 10, 0 to 50, or 0 to 100, for example.

For example, in a particular scaling approach, scaled recurrence score (SRS) is calculated on a scale of 0 to 100. For convenience, 10 Ct units are added to each measured Ct value, and unscaled RS is calculated as described before. Scaled recurrence scores (SRS) are calculated using the equations shown below.

$$GRB7 \text{ Score} = 0.9 \times GRB7 + 0.1 \times HER2$$

$$GRB7 \text{ Threshold Score} = \begin{cases} 8 & \text{if } GRB7 \text{ Score} < 8 \\ GRB7 \text{ Score} & \text{otherwise} \end{cases}$$

$$ER \text{ Score} = (0.8 \times Esr1 + 1.2 \times PR + Bcl2 + CEGP1)/4$$

$$\text{Proliferation Score} = \left( \frac{SURV + Ki\text{-}67 + MYB12 +}{CCNB1 + STK15} \right) / 5$$

Prolif. Threshold Score =

$$\begin{cases} 6.5 & \text{if Proliferation Score} < 6.5 \\ \text{Proliferation Score} & \text{otherwise} \end{cases}$$

$$\text{Invasion Score} = (CTSL2 + STYM3)/2$$

$$SRS = \begin{cases} 0 & \text{if } 20 \times (RS - 6.7) < 0 \\ 100 & \text{if } 20 \times (RS - 6.7) > 100 \\ 20 \times (RS - 6.7) & \text{otherwise} \end{cases}$$

where $$RS = 0.47 \times GRB7 \text{ Group Threshold Score} -$$
$$0.34 \times ER \text{ Group Score} + 1.04 \times \text{Proliferation Group Threshold Score} +$$
$$0.10 \times \text{Invasion Group Score} + 0.05 \times CD68 -$$
$$0.08 \times GSTM1 - 0.07 \times BAG1 \text{ old Score}$$

Patients assigned to various risk categories using the following recurrence scores:

| Risk Category | Recurrence Score |
|---|---|
| Low Risk of Recurrence | RS < 18 |
| Intermediate Risk | 18 ≦ RS < 31 |
| High Risk of Recurrence | RS ≧ 31 |

Figure 2:
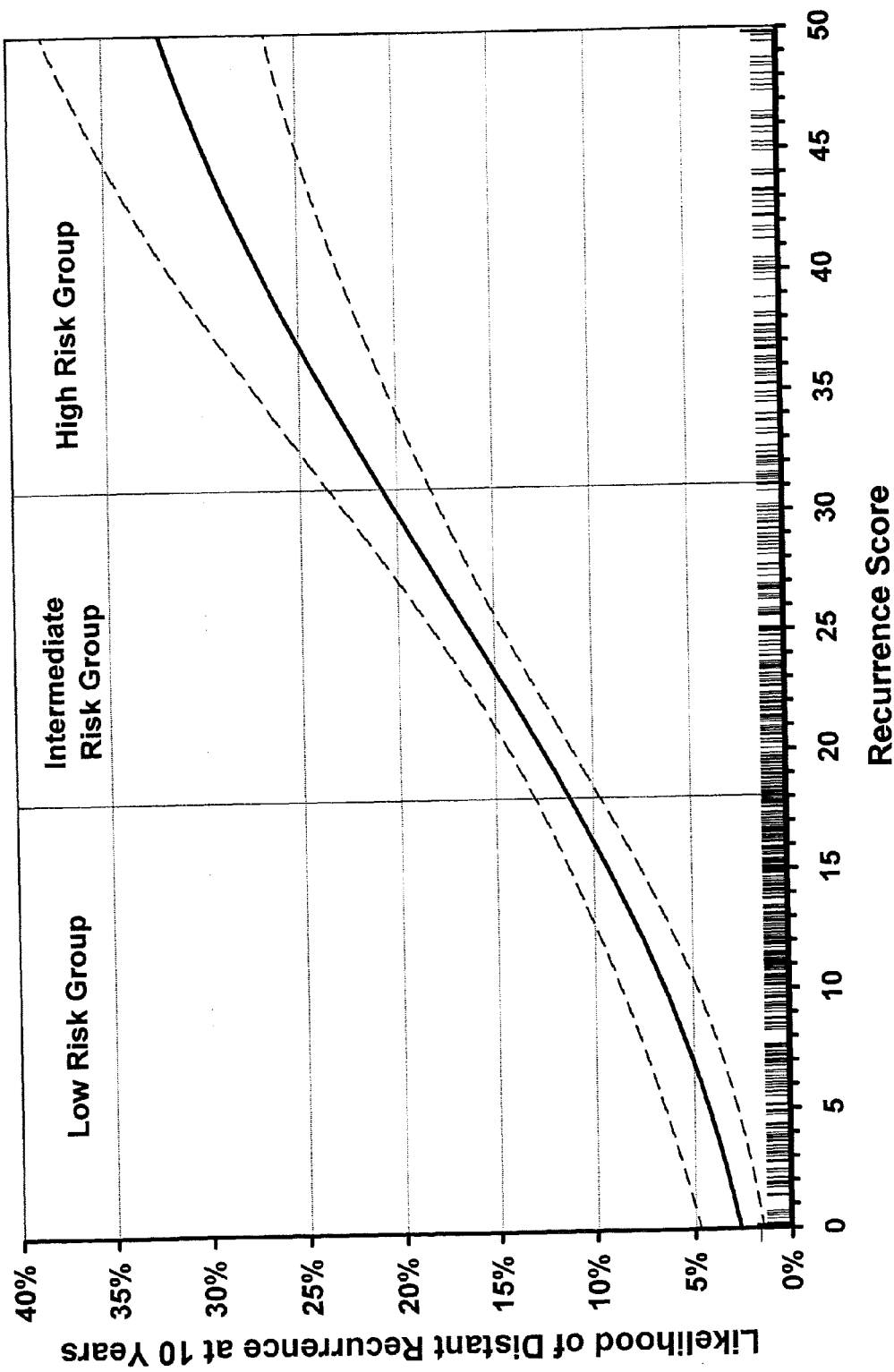
FIG. 2 illustrates the relationship between recurrence score {RS} and rate or likelihood of distant recurrence of breast cancer in 10 years. Data are taken from the NSABP B-14 patient population. Broken lines represent 95% confidence intervals. Each tick mark on the X-axis denotes a patient having the corresponding RS.

This scaled approach was used to calculated the recurrence scores shown in FIG. 2.

10. Use the Recurrence and Response to Treatment Scores

Recurrence scores (RSs) or response to treatment scores (RTS), as determined by the algorithm of the present invention, provide valuable tools for the practicing physician to make critical treatment decisions. Thus, if the RS of a particular patient is low, the physician might decide that chemotherapy following surgical removal of cancer, e.g. breast cancer is not necessary in order to ensure long term survival of patient. As a result, the patient will not be subject to the often very severe side effects of standard of care chemotherapeutic treatment. If, on the other hand, the RS is determined to be high, this information can be used to decide which chemotherapeutic or other treatment option (such as, radiation therapy) is most suitable for treating the patient. Similarly, if the RTS score of a patient for a particular treatment is low, other, more effective, treatment modalities will be used to combat cancer in that particular patient.

By way of example, current standard of care chemotherapeutic options for the treatment of breast cancer include the administration of anthracyclines plus cyclophosphamide (AC); or AC plus a taxanes (ACT); or C plus methotrexate plus 5-fluorouracil (CMF); or the administration of any of these drugs alone, or in any combination. Other chemotherapeutic drugs often used in cancer, e.g. breast cancer, treatment include, for example, Herceptin®, vinblastine, actinomycin D, etoposide, cisplatin, and doxorubicin. Determining the RS for a particular patient by the algorithm of the present invention will enable the physician to tailor the treatment of the patient such that the patient has the best chance of long term survival while unwanted side-effects are minimized.

Thus, patients with a low risk of cancer recurrence are typically assigned to hormonal treatment alone, or hormonal treatment and a less toxic chemotherapeutic treatment regiment, e.g. using Herceptin®. On the other hand, patients whose risk of cancer recurrence ha been determined to be intermediate or high are typically subjected to more aggressive chemotherapy, such as, for example, anthracycline and/or taxane-based treatment regimens.

The RS value can also be used to decide whether to treat the patient with therapeutic drugs that are currently not part of the main line treatment protocol for a particular cancer, such as, for example, EGFR inhibitors, and/or by other treatment options, such as radiation therapy alone, or before or after chemotherapeutic treatment.

Further details of the invention will be provided in the following non-limiting Examples.

EXAMPLE 1

Algorithm to Predict Breast Cancer Recurrence

The algorithm is based on measurements of the tumor levels of 16 mRNA markers, which were selected by two major criteria: 1) univariate correlation with breast cancer recurrence in the clinical study described below, and 2) implication in tumor pathology as indicated by published scientific literature.

The selected markers indicate roles of several cellular behaviors and pathways in cancer recurrence: e.g., Her2 growth factor; estrogen receptor, proliferation, and invasion. Consistent with current understanding of the molecular pathology of breast cancer, increased levels of mRNAs representing genes in the growth factor, proliferation, and invasion axes correlate with increased risk of recurrence whereas increased levels of mRNAs representing genes in the estrogen receptor axis correlate with reduced risk of recurrence. Relevant genes in these pathways are not only linked by biological function, but also linked by co-expression, as indicated by Pearson correlation coefficients (data not shown). For calculation of Pearson correlation coefficient see, e.g. K. Pearson and A. Lee, *Biometrika* 2:357 (1902).

An algorithm was constructed by weighing the contributions of certain co-expressed genes in the above pathways. The model was iteratively optimized by selection for best correlation to recurrence risk. Model fitting included selection of best genes representing the above functional and co-expression axes and selection for optimal equation coefficients.

In addition, other genes were included that were not tightly correlated in expression to any of the above genes or each other, but which were also found to independently contribute to prediction of cancer recurrence. In view of accumulating evidence in the biomedical literature that tumor macrophages confer poor prognosis in cancer (M. Orre and P. A Rogers *Gynecol. Oncol.* 73: 47-50 [1999]; L. M. Coussens et al. *Cell* 103: 481-90 [2000]; S. Huang et al. *J. Natl. Cancer Inst.* 94:1134-42 [2002]; M. A. Cobleigh et al. *Proceedings of*

A.S.C.O. 22: Abstract 3415 [2003]), the macrophage marker CD68 was also included in the test gene set. Ultimately, a model was identified that included the genes: Grb7; Her2; ER; PR; BC12; CEGP1; SURV; Ki-67; MYBL2; CCNB1; STK15; CTSL2; STMY3; GSTM1; BAG1; CD68.

The algorithm provides a recurrence risk Score (RS). Specifically, RS is derived as follows:
1. Define the GRB7 axis
   GRB7 axis=(0.45 to 1.35)×GRB7+(0.05 to 0.15)×HER2
2. Define the GRB7 axis threshold
   if GRB7axis<−2
   then GRB7GTthresh=−2,
   else GRB7GTthresh=GRB7axis
3. Define the ER axis
   Eraxis=(EstR1+PR+Bcl2+CEGP1)/4, where the individual contributions of the genes listed can be weighted by a factor ranging between 0.5 and 1.5, inclusive.
4. Define the proliferation axis, prolifaxis
   prolifaxis=(SURV+Ki.67+MYBL2+CCNB1+STK15)/5, where the individual contributions of the genes listed can be weighted by a factor between 0.5 and 1.5, inclusive.
5. Define the proliferation axis threshold, prolifaxisthresh
   if prolifaxis<−3.5
   then prolifaxisthresh=−3.5,
   else prolifaxisthresh=prolifaxis
6. Define the invasion axis
   invasionaxis=(CTSL2+STMY3)/2, where the individual contributions of the genes listed can be weighted by a factor between 0.5 and 1.5, inclusive.
7. Calculate the recurrence score (RS)
   RS=(0.23 to 0.70)×GRB7GTthresh−(0.17 to 0.51)×ERaxis+(0.52 to 1.56)×prolifaxisthresh+(0.07 to 0.21)×invasionaxis+(0.03 to 0.15)×CD68−(0.04 to 0.25)×GSTM1−(0.05 to 0.22)×BAG1.

In a particular embodiment, RS is calculated as follows:

RS=0.47×GRB7GTthresh−0.34×ERaxis+1.04× profilaxisthresh+0.14×invasionaxis+0.11×CD68− 0.17×GSTM1−0.15BAG1.

One skilled in the art will understand that other genes can be substituted for the 16 test genes specified above. Broadly, any gene that co-expresses with a gene in the 16 gene test panel, with Pearson correlation coefficient≧0.40 can be substituted for that gene in the algorithm. To replace gene X by the correlated gene Y, one determines the range of values for gene X in the patient population, the range of values for gene Y in the patient population, and applies a linear transform to map the values for gene Y into the corresponding values for gene X. For example, if the range of values for gene X in the patient population is 0 to 10, and the range of values for gene Y in the patient population is 0 to 5, the appropriate transform is to multiply values of gene Y by 2.

By way of example, the following genes that lie within the Her2 amplicon, are some of the genes that can be substituted into the growth factor gene subset: Q9BRT3; TCAP; PNMT; ML64; IPPD; Q9H7G1; Q9HBS1; Q9Y220; PSMD3; and CSF3

By way of example, some of the genes that can be substituted into the proliferation gene subset are: C20.orfl, TOP2A, CDC20, KNSL2, MELK, TK1, NEK2, LMNB1, PTTG1, BUB1, CCNE2, FLJ20354, MCM2, RAD54L, PRO2000, PCNA, Chk1, NME1, TS, FOXM1, AD024, and HNRPAB.

By way of example, some of the genes that can be substituted into the estrogen receptor (ER) subset are: HNF3A, ErbB3, GATA3, BECN1, IGF1R, AKT2, DHPS, BAG1, hENT1, TOP2B, MDM2, CCND1, DKFZp586M0723, NPD009, B.Catenin, IRS1, Bclx, RBM5, PTEN, A.Catenin, KRT18, ZNF217, ITGA7, GSN, MTA1, G.Catenin, DR5, RAD51C, BAD, TP53BP1, RIZ1, IGFBP2, RUNX1, PPM1D, TFF3, S100A8, P28, SFRS5, and IGFBP2.

By way of example, some of the genes that can be substituted into the invasion axis are: upa, COL1A1, COL1A2, and TIMP2.

Some of the genes that can be substituted for CD68 are: CTSB, CD18, CTSL, HLA.DPB1, MMP9.

Some of the genes that can be substituted for GSTM1 are: GSTM3.2, MYH11.1, GSN.3, ID1.1.

Some of the genes that can be substituted for BAG1 are: Bcl2.2, GATA3.3, DHPS.3, HNF3A.1.

The RS values determined can be used guide the binary (yes or no) decision whether to treat lymph node negative breast cancer patients with adjuvant chemotherapy. For this purpose a threshold can be defined separating high from low risk patients. As noted before, it may be more informative to define three categories: high, moderate and low risk, which requires two RS cut points. Cut points can be selected to subgroup patients in desired categories of risk by applying the algorithm to certain clinical study data. For example, oncologists may wish to avoid treating lymph node-negative breast cancer patients who carry a less than 10% risk of recurrence within ten years. Application of the algorithm to the clinical trial data described in Example 2 indicates that patients with RS<−3.9 have less than 10% risk of recurrence in ten years, whereas patients with RS>−3.5 have a greater than 39% risk of recurrence in ten years. Patients with intermediate RS values can be considered in the moderate risk category. Oncologists can be provided with RS results in a continuous figure relating recurrence score to ten year Kaplan Meier survival.

EXAMPLE 2

Study of Gene Expression in 242 Malignant Breast Tumors

A gene expression study was designed and conducted to determine recurrence score (RS) values in a population of patients with node-negative invasive breast cancer and explore the correlation between RS values and disease-free survival. The study utilized archived fixed paraffin-embedded tumor blocks as a source of RNA and matched archived patient records.

Study Design:

Molecular assays were performed on paraffin-embedded, formalin-fixed primary breast tumor tissues obtained from 252 individual patients diagnosed with invasive breast cancer. All patients were lymph node-negative, ER-positive, and treated with Tamoxifen. Mean age was 52 years, and mean clinical tumor size was 2 cm. Median follow-up was 10.9 years. As of Jan. 1, 2003, 41 patients had local or distant disease recurrence or breast cancer death. Patients were included in the study only if histopathologic assessment, performed as described in the Materials and Methods section, indicated adequate amounts of tumor tissue and homogeneous pathology.

Materials and Methods:

Each representative tumor block was characterized by standard histopathology for diagnosis, semi-quantitative assessment of amount of tumor, and tumor grade. When tumor area was less than 70% of the section the tumor area was grossly dissected and tissue was taken from 6 (10 micron) sections. Otherwise, a total of 3 sections (also 10 microns in thickness each) were prepared. Sections were placed in two Costar Brand Microcentrifuge Tubes (Polypropylene, 1.7 mL tubes, clear). If more than one tumor block was obtained as part of the surgical procedure, the block most representative of the pathology was used for analysis. Gene Expression Analysis; mRNA was extracted and purified from fixed, paraffin-embedded tissue samples, and prepared for gene expression analysis as described above. Molecular assays of quantitative gene expression were performed by RT-PCR, using the ABI PRISM 7900™ Sequence Detection System™ (Perkin-Elmer-Applied Biosystems, Foster City, Calif., USA). ABI PRISM 7900™ consists of a thermocycler, laser, charge-coupled device (CCD), camera and computer. The system amplifies samples in a 384-well format on a thermocycler. The system includes software for running the instrument and for analyzing the data.

Figure 1B:
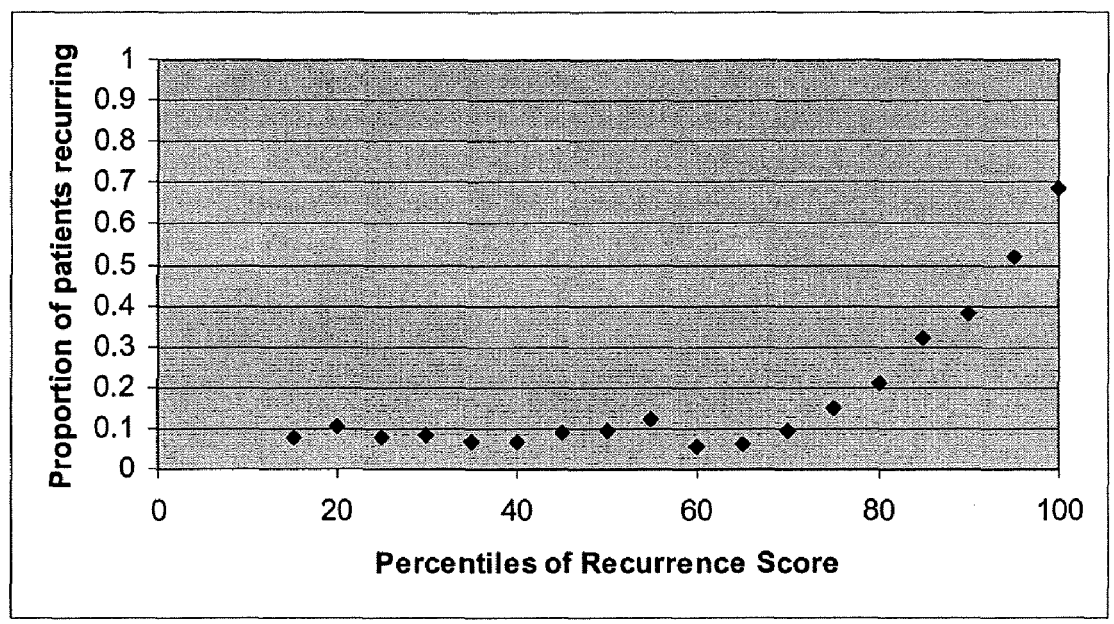
FIG. 1B is similar to FIG. 1A. It also presents proportion of patients with actual cancer recurrence, but in this case the actual recurrence data are plotted against percentiles of recurrence scores. Patients are grouped in 5 percentile units, except for patients in the lower 20 percentile, who are all grouped together.

Results:

Normalized gene expression values were obtained from the above patient specimens and used to calculate RS for each patient, which was matched with respective Kaplan-Meier 10 year survival data as shown in FIGS. 1A and B. As shown, patients with RS values less than approximately −3.75 have ~90% chance of 10 year recurrence-free survival. Recurrence rates rise sharply at RS values>−3.3. At RS~−3.0 risk of recurrence in 10 years is about 30%, and at RS~−2.0 risk of recurrence in 10 years is >50%. FIG. 1B reveals that approximately 70% of patients are in the lowest risk category.

The results thus demonstrate a close correspondence between RS values as determined by the described test and algorithm and the risk of breast cancer recurrence.

EXAMPLE 3

Validation of the Algorithm of the Invention

A prospective clinical validation study was conducted to examine the performance of a multi-gene RT-PCR assay for extracting and quantifying RNA from fixed paraffin embedded tumor tissue in patients enrolled in the tamoxifen alone arm of the National Surgical Adjuvant Breast and Bowel Project (NSABP)

Study B-14: A Laboratory Study To Clinically Validate Whether Genomic Tumor Expression Profiles Can Define The Likelihood Of Recurrence In Patients With Primary Invasive Breast Cancer, Negative Axillary Nodes And Estrogen-Receptor Positive Tumors. The NSABP Study B-14 was conducted to assess the efficacy of post-mastectomy tamoxifen treatment in node-negative primary breast cancer patients and included a total of 2,892 patients who qualified and were treated for five years. The protocol was carried out in a randomized, double-blind manner with one set of patients receiving tamoxifen at a dose of 10 mg twice a day and a control set of patients receiving physically identical placebo tablets. Comparisons of the multi-gene assay to standard histopathologic and molecular measures of tumor classification were performed.

Patient specific recurrence scores derived from the multi-gene assay were obtained for a total of 668 eligible patients from the tamoxifen alone arm of the NSABP Study B-14 (median follow-up time, 14.1 years). Statistical analyses revealed that the resulting patient specific recurrence scores (FIG. 2) are significantly ($P=6.5$ E-9) correlated to the likelihood of distant recurrence and provide significant information beyond standard clinical measures of tumor classification, including patient age at surgery, clinical tumor size and tumor grade.

It was found that the assay and algorithm of the present invention provide reproducible and informative measures of the likelihood of distant recurrence from tumor tissue collected at the time of surgery for node-negative, ER+, primary breast cancer patients treated with tamoxifen. The patient recurrence score generated by the method of the present invention provides significant ($P<0.0001$) information beyond standard histopathologic and molecular measures of tumor classification commonly used in clinical practice, including age, clinical tumor size and tumor grade. In contrast to other commonly clinical measures, the patient recurrence score is highly reproducible and unlike other molecular tests simultaneously leverages information across multiple genomic markers, including ER, PR and HER2.

While the present invention has been described with reference to what are considered to be the specific embodiments, it is to be understood that the invention is not limited to such embodiments. To the contrary, the invention is intended to cover various modifications and equivalents included within the spirit and scope of the appended claims. For example, while the disclosure focuses on the identification of various breast cancer associated genes and gene sets, and on the personalized prognosis of breast cancer, similar genes, gene sets and methods concerning other types of cancer are specifically within the scope herein.

All references cited throughout the disclosure are hereby expressly incorporated by reference.

TABLE 1

| Gene | Accession No. | Name | Artificial Sequence PCR Primer-Probe | Sequence | Length |
| --- | --- | --- | --- | --- | --- |
| B-actin | NM_001101 | S0034/B-acti.f2 | SEQ ID NO: 1 | CAGCAGATGTGGATCAGCAAG | 21 |
| B-actin | NM_001101 | S0036/B-acti.r2 | SEQ ID NO: 2 | GCATTTGCGGTGGACGAT | 18 |
| B-actin | NM_001101 | S4730/B-acti.p2 | SEQ ID NO: 3 | AGGAGTATGACGAGTCCGGCCCC | 23 |
| BAG1 | NM_004323 | S1386/BAG1.f2 | SEQ ID NO: 4 | CGTTGTCAGCACTTGGAATACAA | 23 |
| BAG1 | NM_004323 | S1387/BAG1.r2 | SEQ ID NO: 5 | GTTCAACCTCTTCCTGTGGACTGT | 24 |
| BAG1 | NM_004323 | S4731/BAG1.p2 | SEQ ID NO: 6 | CCCAATTAACATGACCCGGCAACCAT | 26 |
| Bcl2 | NM_000633 | S0043/Bcl2.f2 | SEQ ID NO: 7 | CAGATGGACCTAGTACCCACTGAGA | 25 |
| Bcl2 | NM_000633 | S0045/Bcl2.r2 | SEQ ID NO: 8 | CCTATGATTTAAGGGCATTTTTCC | 24 |
| Bcl2 | NM_000633 | S4732/Bcl2.p2 | SEQ ID NO: 9 | TTCCACGCCGAAGGACAGCGAT | 22 |

TABLE 1-continued

| Gene | Accession No. | Name | Artificial Sequence PCR Primer-Probe Sequence | | Length |
|---|---|---|---|---|---|
| CCNB1 | NM_031966 | S1720/CCNB1.f2 | SEQ ID NO: 10 | TTCAGGTTGTTGCAGGAGAC | 20 |
| CCNB1 | NM_031966 | S1721/CCNB1.r2 | SEQ ID NO: 11 | CATCTTCTTGGGCACACAAT | 20 |
| CCNB1 | NM_031966 | S4733/CCNB1.p2 | SEQ ID NO: 12 | TGTCTCCATTATTGATCGGTTCATGCA | 27 |
| CD68 | NM_001251 | S0067/CD68.f2 | SEQ ID NO: 13 | TGGTTCCCAGCCCTGTGT | 18 |
| CD68 | NM_001251 | S0069/CD68.r2 | SEQ ID NO: 14 | CTCCTCCACCCTGGGTTGT | 19 |
| CD68 | NM_001251 | S4734/CD68.p2 | SEQ ID NO: 15 | CTCCAAGCCCAGATTCAGATTCGAGTCA | 28 |
| CEGP1 | NM_020974 | S1494/CEGP1.f2 | SEQ ID NO: 16 | TGACAATCAGCACACCTGCAT | 21 |
| CEGP1 | NM_020974 | S1495/CEGP1.r2 | SEQ ID NO: 17 | TGTGACTACAGCCGTGATCCTTA | 23 |
| CEGP1 | NM_020974 | S4735/CEGP1.p2 | SEQ ID NO: 18 | CAGGCCCTCTTCCGAGCGGT | 20 |
| CTSL2 | NM_001333 | S4354/CTSL2.f1 | SEQ ID NO: 19 | TGTCTCACTGAGCGAGCAGAA | 21 |
| CTSL2 | NM_001333 | S4355/CTSL2.r1 | SEQ ID NO: 20 | ACCATTGCAGCCCTGATTG | 19 |
| CTSL2 | NM_001333 | S4356/CTSL2.p1 | SEQ ID NO: 21 | CTTGAGGACGCGAACAGTCCACCA | 24 |
| EstR1 | NM_000125 | S0115/EstR1.f1 | SEQ ID NO: 22 | CGTGGTGCCCCTCTATGAC | 19 |
| EstR1 | NM_000125 | S0117/EstR1.r1 | SEQ ID NO: 23 | GGCTAGTGGGCGCATGTAG | 19 |
| EstR1 | NM_000125 | S4737/EstR1.p1 | SEQ ID NO: 24 | CTGGAGATGCTGGACGCCC | 19 |
| GAPDH | NM_002046 | S0374/GAPDH.f1 | SEQ ID NO: 25 | ATTCCACCCATGGCAAATTC | 20 |
| GAPDH | NM_002046 | S0375/GAPDH.r1 | SEQ ID NO: 26 | GATGGGATTTCCATTGATGACA | 22 |
| GAPDH | NM_002046 | S4738/GAPDH.p1 | SEQ ID NO: 27 | CCGTTCTCAGCCTTGACGGTGC | 22 |
| GRB7 | NM_005310 | S0130/GRB7.f2 | SEQ ID NO: 28 | ccatctgcatccatcttgtt | 20 |
| GRB7 | NM_005310 | S0132/GRB7.r2 | SEQ ID NO: 29 | ggccaccagggtattatctg | 20 |
| GRB7 | NM_005310 | S4726/GRB7.p2 | SEQ ID NO: 30 | ctccccacccttgagaagtgcct | 23 |
| GSTM1 | NM_000561 | S2026/GSTM1.r1 | SEQ ID NO: 31 | GGCCCAGCTTGAATTTTTCA | 20 |
| GSTM1 | NM_000561 | S2027/GSTM1.f1 | SEQ ID NO: 32 | AAGCTATGAGGAAAAGAAGTACACGAT | 27 |
| GSTM1 | NM_000561 | S4739/GSTM1.p1 | SEQ ID NO: 33 | TCAGCCACTGGCTTCTGTCATAATCAGGAG | 30 |
| GUS | NM_000181 | S0139/GUS.f1 | SEQ ID NO: 34 | CCCACTCAGTAGCCAAGTCA | 20 |
| GUS | NM_000181 | S0141/GUS.r1 | SEQ ID NO: 35 | CACGCAGGTGGTATCAGTCT | 20 |
| GUS | NM_000181 | S4740/GUS.p1 | SEQ ID NO: 36 | TCAAGTAAACGGGCTGTTTTCCAAACA | 27 |
| HER2 | NM_004448 | S0142/HER2.f3 | SEQ ID NO: 37 | CGGTGTGAGAAGTGCAGCAA | 20 |
| HER2 | NM_004448 | S0144/HER2.r3 | SEQ ID NO: 38 | CCTCTCGCAAGTGCTCCAT | 19 |
| HER2 | NM_004448 | S4729/HER2.p3 | SEQ ID NO: 39 | CCAGACCATAGCACACTCGGGCAC | 24 |
| Ki-67 | NM_002417 | S0436/Ki-67.f2 | SEQ ID NO: 40 | CGGACTTTGGGTGCGACTT | 19 |
| Ki-67 | NM_002417 | S0437/Ki-67.r2 | SEQ ID NO: 41 | TTACAACTCTTCCACTGGGACGAT | 24 |
| Ki-67 | NM_002417 | S4741/Ki-67.p2 | SEQ ID NO: 42 | CCACTTGTCGAACCACCGCTCGT | 23 |
| MYBL2 | NM_002466 | S3270/MYBL2.f1 | SEQ ID NO: 43 | GCCGAGATCGCCAAGATG | 18 |
| MYBL2 | NM_002466 | S3271/MYBL2.r1 | SEQ ID NO: 44 | CTTTTGATGGTAGAGTTCCAGTGATTC | 27 |
| MYBL2 | NM_002466 | S4742/MYBL2.p1 | SEQ ID NO: 45 | CAGCATTGTCTGTCCTCCCTGGCA | 24 |
| PR | NM_000926 | S1336/PR.f6 | SEQ ID NO: 46 | GCATCAGGCTGTCATTATGG | 20 |
| PR | NM_000926 | S1337/PR.r6 | SEQ ID NO: 47 | AGTAGTTGTGCTGCCCTTCC | 20 |

TABLE 1-continued

| Gene | Accession No. | Name | Artificial Sequence PCR Primer-Probe Sequence | Length |
|---|---|---|---|---|
| PR | NM_000926 | S4743/PR.p6 | SEQ ID NO: 48 TGTCCTTACCTGTGGGAGCTGTAAGGTC | 28 |
| RPLPO | NM_001002 | S0256/RPLPO.f2 | SEQ ID NO: 49 CCATTCTATCATCAACGGGTACAA | 24 |
| RPLPO | NM_001002 | S0258/RPLPO.r2 | SEQ ID NO: 50 TCAGCAAGTGGGAAGGTGTAATC | 23 |
| RPLPO | NM_001002 | S4744/RPLPO.p2 | SEQ ID NO: 51 TCTCCACAGACAAGGCCAGGACTCG | 25 |
| STK15 | NM_003600 | S0794/STK15.f2 | SEQ ID NO: 52 CATCTTCCAGGAGGACCACT | 20 |
| STK15 | NM_003600 | S0795/STK15.r2 | SEQ ID NO: 53 TCCGACCTTCAATCATTTCA | 20 |
| STK15 | NM_003600 | S4745/STK15.p2 | SEQ ID NO: 54 CTCTGTGGCACCCTGGACTACCTG | 24 |
| STMY3 | NM_005940 | S2067/STMY3.f3 | SEQ ID NO: 55 CCTGGAGGCTGCAACATACC | 20 |
| STMY3 | NM_005940 | S2068/STMY3.r3 | SEQ ID NO: 56 TACAATGGCTTTGGAGGATAGCA | 23 |
| STMY3 | NM_005940 | S4746/STMY3.p3 | SEQ ID NO: 57 ATCCTCCTGAAGCCCTTTTCGCAGC | 25 |
| SURV | NM_001168 | S0259/SURV.f2 | SEQ ID NO: 58 TGTTTTGATTCCCGGGCTTA | 20 |
| SURV | NM_001168 | S0261/SURV.r2 | SEQ ID NO: 59 CAAAGCTGTCAGCTCTAGCAAAAG | 24 |
| SURV | NM_001168 | S4747/SURV.p2 | SEQ ID NO: 60 TGCCTTCTTCCTCCCTCACTTCTCACCT | 28 |
| TFRC | NM_003234 | S1352/TFRC.f3 | SEQ ID NO: 61 GCCAACTGCTTTCATTTGTG | 20 |
| TFRC | NM_003234 | S1353/TFRC.r3 | SEQ ID NO: 62 ACTCAGGCCCATTTCCTTTA | 20 |
| TFRC | NM_003234 | S4748/TFRC.p3 | SEQ ID NO: 63 AGGGATCTGAACCAATACAGAGCAGACA | 28 |

TABLE 2

| Gene | Accession No. | Artificial Sequence PCR Amplicon | Amplicon Sequence |
|---|---|---|---|
| B-actin | NM_001101 | | SEQ ID NO: 64 CAGCAGATGTGGATCAGCAAGCAGGAGTATGACGAGTCCGGCCCCTCCATCGTCCACCGCAATGC |
| BAG1 | NM_004323 | | SEQ ID NO: 65 CGTTGTCAGCACTTGGAATACAAGATGGTTGCCGGGTCATGTTAATTGGGAAAAAGAACAGTCCACAGGAAGAGGTTGAAC |
| Bcl2 | NM_000633 | | SEQ ID NO: 66 CAGATGGACCTAGTACCCACTGAGATTTCCACGCCGAAGGACAGCGATGGGAAAAATGCCCTTAAATCATAGG |
| CCNB1 | NM_031966 | | SEQ ID NO: 67 TTCAGGTTGTTGCAGGAGACCATGTACATGACTGTCTCCATTATTGATCGGTTCATGCAGAATAATTGTGTGCCCAAGAAGATG |
| CD68 | NM_001251 | | SEQ ID NO: 68 TGGTTCCCAGCCCTGTGTCCACCTCCAAGCCCAGATTCAGATTCGAGTCATGTACACAACCCAGGGTGGAGGAG |
| CEGP1 | NM_020974 | | SEQ ID NO: 69 TGACAATCAGCACACCTGCATTCACCGCTCGGAAGAGGGCCTGAGCTGCATGAATAAGGATCACGGCTGTAGTCACA |
| CTSL2 | NM_001333 | | SEQ ID NO: 70 TGTCTCACTGAGCGAGCAGAATCTGGTGGACTGTTCGCGTCCTCAAGGCAATCAGGGCTGCAATGGT |
| EstR1 | NM_000125 | | SEQ ID NO: 71 CGTGGTGCCCCTCTATGACCTGCTGCTGGAGATGCTGGACGCCCACCGCCTACATGCGCCCACTAGCC |
| GAPDH | NM_002046 | | SEQ ID NO: 72 ATTCCACCCATGGCAAATTCCATGGCACCGTCAAGGCTGAGAACGGGAAGCTTGTCATCAATGGAAATCCCATC |
| GRB7 | NM_005310 | | SEQ ID NO: 73 CCATCTGCATCCATCTTGTTTGGGCTCCCCACCCTTGAGAAGTGCCTCAGATAATACCCTGGTGGCC |
| GSTM1 | NM_000561 | | SEQ ID NO: 74 AAGCTATGAGGAAAAGAAGTACACGATGGGGGACGCTCCTGATTATGACAGAAGCCAGTGGCTGAATGAAAAAATTCAAGCTGGGCC |
| GUS | NM_000181 | | SEQ ID NO: 75 CCCACTCAGTAGCCAAGTCACAATGTTTGGAAAACAGCCCGTTTACTTGAGCAAGACTGATACCACCTGCGTG |
| HER2 | NM_004448 | | SEQ ID NO: 76 CGGTGTGAGAAGTGCAGCAAGCCCTGTGCCCGAGTGTGCTATGGTCTGGGCATGGAGCACTTGCGAGAGG |

TABLE 2-continued

| Gene | Accession No. | Artificial Sequence PCR Amplicon | Amplicon Sequence |
|---|---|---|---|
| Ki-67 | NM_002417 | SEQ ID NO: 77 | CGGACTTTGGGTGCGACTTGACGAGCGGTGGTTCGACAAGTGGCCTTGCGGGCCGGATCGTCCCAGTGGAAGAGTTGTAA |
| MYBL2 | NM_002466 | SEQ ID NO: 78 | GCCGAGATCGCCAAGATGTTGCCAGGGAGGACAGACAATGCTGTGAAGAATCACTGGAACTCTACCATCAAAAG |
| PR | NM_000926 | SEQ ID NO: 79 | GCATCAGGCTGTCATTATGGTGTCCTTACCTGTGGGAGCTGTAAGGTCTTCTTTAAGAGGGCAATGGAAGGGCAGCACAACTACT |
| RPLPO | NM_001002 | SEQ ID NO: 80 | CCATTCTATCATCAACGGGTACAAACGAGTCCTGGCCTTGTCTGTGGAGACGGATTACACCTTCCCACTTGCTGA |
| STK15 | NM_003600 | SEQ ID NO: 81 | CATCTTCCAGGAGGACCACTCTCTGTGGCACCCTGGACTACCTGCCCCCTGAAATGATTGAAGGTCGGA |
| STMY3 | NM_005940 | SEQ ID NO: 82 | CCTGGAGGCTGCAACATACCTCAATCCTGTCCCAGGCCGGATCCTCCTGAAGCCCTTTTCGCAGCACTGCTATCCTCCAAAGCCATTGTA |
| SURV | NM_001168 | SEQ ID NO: 83 | TGTTTTGATTCCCGGGCTTACCAGGTGAGAAGTGAGGGAGGAAGAAGGCAGTGTCCCTTTTGCTAGAGCTGACAGCTTTG |
| TFRC | NM_003234 | SEQ ID NO: 84 | GCCAACTGCTTTCATTTGTGAGGGATCTGAACCAATACAGAGCAGACATAAAGGAAATGGGCCTGAGT |

What is claimed is:

1. A method for determining the likelihood of breast cancer recurrence or response to hormonal therapy in a human subject comprising:
   (a) measuring the expression levels of the RNA transcripts of SURV, Ki.67, MYBL2, CCNB1, STK15, CTSL2, and STMY3, or their expression products, in a biological sample containing tumor cells obtained from said subject;
   (b) calculating a recurrence score (RS) for said subject by weighting the measured expression levels of gene subsets by contribution to breast cancer recurrence, wherein the gene subsets comprise:
      (i) a proliferation subset: SURV, Ki.67, MYBL2, CCNB1, and STK15; and
      (ii) an invasion subset: CTSL2, and STMY3;
   and
   (c) creating a report providing the RS;

wherein the RS is indicative of the likelihood of breast cancer recurrence in said subject or response of said subject to hormonal therapy.

2. The method of claim 1, wherein the expression of the genes SURV, K167, MYBL2, CCNB1, STK15, CTSL2, and STMY3 is measured by determining protein expression levels.

3. The method of claim 1, further comprising measuring the expression levels of RNA transcripts of CD68, GSTM1 and BAG1 or their expression products, or corresponding substitute genes or their expression products, and including the contribution of the measured expression levels of the genes or substitute genes to breast cancer recurrence in calculating the RS,
wherein a higher RS represents an increased likelihood of breast cancer recurrence, and
wherein a corresponding substitute gene for CD68 is selected from the group consisting of CTSB, CD18, CTSL, HLA.DPB1, and MMP9, a corresponding substitute gene for GSTM1 is selected from the group consisting of GSTM2, GSTM3, GSTM4, GSTM5, MYH11, GSN, and ID1, and a corresponding substitute gene for BAG1 is selected from the group consisting of Bcl2, GATA3, DHPS, and HNF3A.

4. The method of claim 3, wherein the expression of the genes SURV, K167, MYBL2, CCNB1, STK15, CTSL2, STMY3, CD68, GSTM1, and BAG1 is measured by determining protein expression levels.

5. The method of claim 1, wherein the cancer is lymph node negative breast cancer.

6. The method of claim 1, wherein the individual contribution of each gene of gene subsets (i) and (ii) is weighted separately.

7. The method of claim 1, comprising weighting equally the individual contributions of the genes listed in gene subset (i), or their expression products, to breast cancer recurrence.

8. The method of claim 1, comprising weighting equally the individual contributions of the genes listed in gene subset (ii), or their expression products, to breast cancer recurrence.

9. The method of claim 1, wherein increased levels of the RNA transcripts of the genes in gene subsets (i) and (ii), or their expression products, are associated with increased risk of breast cancer recurrence, and are assigned a positive value.

10. The method of claim 3, wherein increased level of the RNA transcript of CD68, or its expression product, is associated with increased risk of breast cancer recurrence, and is assigned a positive value.

11. The method of claim 3, wherein increased levels of the RNA transcripts of GSTM1 and BAG1, or their expression products, are associated with decreased risk of breast cancer recurrence, and are assigned a negative value.

12. The method of claim 1, wherein said biological sample is selected from the group consisting of fresh tumor tissue, fine needle aspirates, peritoneal fluid, ductal lavage and pleural fluid.

13. The method of claim 1, wherein said biological sample is obtained from a fixed, paraffin embedded tumor tissue.

14. The method of claim 13, wherein said tissue has been obtained by biopsy.

15. The method of claim 1, wherein the expression levels of said RNA transcripts are determined by reverse transcription-polymerase chain reaction.

16. The method of claim 1, wherein said RNA is fragmented.

17. A method for determining a likelihood of breast cancer recurrence or response to hormonal therapy in a human subject comprising:

a. measuring expression levels of RNA transcripts for a plurality of genes, or their expression products, in a biological sample containing tumor cells obtained from the subject,
wherein the plurality of genes are grouped in gene subsets comprising:
(i) SURV, Ki.67, MYBL2, CCNB1, and STK15; and
(ii) CTSL2, and STMY3,
wherein at least one gene within subset (i) may be replaced by a substitute gene from a group consisting of C20.orfl, TOP2A, CDC20, KNSL2, MELK, TK1, NEK2, LMNB1, PTTG1, BUB1, CCNE2, F1120354, MCM2, RAD54L, PRO2000, PCNA, Chk1, NME1, TS, FOXM1, AD024, and HNRPAB,
b. calculating a recurrence score (RS) for the subject by weighting of the measured expression levels for each of the gene subsets by contribution to breast cancer recurrence; and
c. creating a report which includes the RS;
wherein the RS is indicative of a likelihood of breast cancer recurrence or response to therapy in said human subject.

18. The method of claim 17, further comprising
measuring expression levels of RNA transcripts of CD68, GSTM1 and BAG1, or a substitute gene thereof, or their expression products, and including the contribution of measured expression levels of CD68, GSTM1 and BAG1, or substitute genes, to breast cancer recurrence in calculating the RS,
wherein a higher RS represents an increased likelihood of breast cancer recurrence,
wherein a substitute gene for CD68 is selected from the group consisting of CTSB, CD18, CTSL, HLA.DPB1, and MMP9,
wherein a substitute gene for GSTM1 is selected from the group consisting of GSTM2, GSTM3, GSTM4, GSTM5, MYH11, GSN, and ID1, and
wherein a substitute gene for BAG1 is selected from the group consisting of Bcl2, GATA3, DHPS, and HNF3A.

19. The method of claim 18, wherein an increased level of a RNA transcript of CD68 or a substitute gene, or its expression product, is associated with an increased risk of breast cancer recurrence, and is assigned a positive value.

20. The method of claim 18, wherein increased levels of RNA transcripts of GSTM1 and BAG1, or a substitute gene thereof, or their expression products, are associated with a decreased risk of breast cancer recurrence, and are assigned a negative value.

21. The method of claim 17, wherein the cancer is lymph node negative breast cancer.

22. The method of claim 17, wherein the contributions of gene subset (i) is included at a threshold value until the contributions exceed the threshold value, at which point the contributions are included as a total expression level of the RNA transcripts of the genes or substitute genes in said subsets, or their expression products.

23. The method of claim 17, wherein, within each of gene subset (ii), individual contributions of each gene or substitute gene included is weighted separately.

24. The method of claim 17, comprising weighting equally individual contributions of the genes or substitute genes of gene subset (i), or their expression products, to breast cancer recurrence.

25. The method of claim 17, comprising weighting equally individual contributions of each gene or substitute gene of gene subset (ii), or their expression products, to breast cancer recurrence.

26. The method of claim 17, wherein increased levels of RNA transcripts of the genes or substitute genes of gene subsets (i) and (ii), or their expression products, are associated with increased risk of breast cancer recurrence, and are assigned a positive value.

27. The method of claim 17, wherein the contributions of gene subset (i) is included at a threshold value until the contributions exceed the threshold value, at which point the contributions are included as a total expression level of the RNA transcripts of the genes in said subsets, or their expression products.

28. The method of claim 18, wherein the expression of the genes SURV, K167, MYBL2, CCNB1, STK15, CTSL2, STMY3, CD68, GSTM1, and BAG1 is measured by determining protein expression levels.

29. The method of claim 17, wherein the expression levels of said RNA transcripts are determined by reverse transcription-polymerase chain reaction.

* * * * *